(12) United States Patent
Manucharyan et al.

(10) Patent No.: US 8,394,380 B2
(45) Date of Patent: *Mar. 12, 2013

(54) COMPOSITIONS AND METHODS FOR ALZHEIMER'S DISEASE

(75) Inventors: Karen Manucharyan, Coyoacan (MX); Gohar Gevorgyan, Coyoacan (MX)

(73) Assignee: Primex Clinical Laboratories, Inc., Van Nuys, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/945,669

(22) Filed: Nov. 12, 2010

(65) Prior Publication Data

US 2011/0065654 A1 Mar. 17, 2011

Related U.S. Application Data

(60) Division of application No. 11/773,349, filed on Jul. 3, 2007, now Pat. No. 7,846,892, which is a division of application No. 10/902,546, filed on Jul. 29, 2004, now abandoned, which is a continuation-in-part of application No. 10/895,224, filed on Jul. 20, 2004, now abandoned.

(51) Int. Cl.
*A61K 39/395* (2006.01)
(52) U.S. Cl. ............... 424/135.1; 424/134.1; 424/139.1; 424/142.1
(58) Field of Classification Search ................. None
See application file for complete search history.

(56) References Cited

U.S. PATENT DOCUMENTS

| | | | |
|---|---|---|---|
| 4,946,778 A * | 8/1990 | Ladner et al. ............ | 435/69.6 |
| 5,223,409 A | 6/1993 | Ladner et al. | |
| 5,622,699 A | 4/1997 | Ruoslahti et al. | |
| 5,786,324 A | 7/1998 | Gray et al. | |
| 6,068,829 A | 5/2000 | Ruoslahti et al. | |
| 6,703,015 B1 | 3/2004 | Solomon et al. | |
| 6,743,427 B1 | 6/2004 | Schenk | |
| 2003/0223996 A1 | 12/2003 | Ruben et al. | |
| 2004/0082762 A1 | 4/2004 | Basi et al. | |
| 2004/0086520 A1 | 5/2004 | Diamond | |
| 2009/0297505 A1* | 12/2009 | Davies et al. ............ | 424/130.1 |

FOREIGN PATENT DOCUMENTS

WO WO0162801 8/2001

OTHER PUBLICATIONS

Cai J et al. Screening and characterization of human single-chain Fv antibody against beta-amyloid peptide 40. NeuroReport, Feb. 2003; 14(2):265-268.*
Manoutcharian K et al. Amyloid-beta peptide-specific single chain Fv antibodies isoloated from an immune phage display library. J. Neuroimmunol. Dec. 2003; 145:12-17.*
Patel, Journal of Geriatric Psychiatry and Neurology, vol. 8, 81-95, 1995.
Kar et al., J. Psychiatry Neurosci., vol. 29(6), pp. 427-441, 2004.
Kasim et al., Alanine-Scanning of hte 50's Loop in the *Clostridium beijerinchii* Flavodoxin: Evaluation of Additivity and the importance of Interactions Provided by the Main Chain in the Modulation of the Oxidation, Biochemistry, vol. 40, pp. 13548-13555, 2001.
Cai et al., Screening and characterization of human single-chain Fv antibody against Beta-amyloid peptide 40, Neuroreport, vol. 14, pp. 265-268, Feb. 10, 2003.
Vickers, "A Vaccine Against Alzheimer's Disease," Drugs Aging, vol. 19, pp. 487-494, 2002.
Solomon, "Anti-Aggregating Antibodies, a New Approach Towards Treatment of Conformational Diseases," Current Medicinal Chemistry, vol. 9, No. 19, pp. 1737-1749, 2002.
Schenk, "Amyloid-B immunotherapy for Alzheimer's disease: the end of the beginning," Nature Reviews, Neuroscience, vol. 3, pp. 824-828, Oct. 2002.
Bacskai et al.; Non-Fc-Mediated Mechanisms Are Involved in Clearance of Amyloid-β in vivo by Immunotherapy; J. Neuroscience; 2002; v. 22; pp. 7873-7878.
Bard et al.; Peripherally administered antibodies against amyloid-β peptide enter the central nervous system and reduce pathology in a mouse model of Alzheimer disease; Nat. Med.; 2000; v. 6, No. 8;pp. 916-919.
Bastianetto et al.; The *Ginkgo biloba* Extract (EGb 761) Protects and Rescues Hippocampal Cells Against Nitric-Oxide-Induced Toxicity: Involvement of Its Flavonoid Constituents and Protein Kinase C; J. Neurochem; 2000; v. 74, pp. 2268-2277.
Bitan et al.; Amyloid β-protein (Aβ) assembly: Aβ40 and Aβ42 oligomerize through distinct pathways; Proc. Natl. Acad. Sci.; 2003; v. 100, No. 1; pp. 330-335.
Bourgeois et al.; Prophylactic Administration of a Complementarity-Determining Region Derived from a Neutralizing Monoclonal Antibody Is Effective against Respiratory Syncytial Virus Infection in BALB/c Mice; J. Virol.; 1998; v. 72, No. 1; pp. 807-810.
Brewer et al.; Optimized Survival of Hippocampal Neurons in B27-Supplemented Neurobasal™, a New Serum-free Medium Combination ; J. Neurosci. Res.; 1993; v. 35; pp. 567-576.
Calhoun et al.; Neuronal overexpression of mutant amyloid precursor protein results in prominent deposition of cerebrovascular amyloid; Proc. Natl. Acad. Sci.; 1999; v. 96; pp. 14088-14093.
Das et al.; Amyloid-β Immunization Effectively Reduces Amyloid Deposition in FcRγ-/- Knock-Out Mice; J. Neuroscience; 2003; v. 23; pp. 8532-8538.
Demattos et al.; Peripheral anti-Aβ antibody alters CNS and plasma Aβ clearance and decreases brain Aβ burden in a mouse model of Alzheimer's disease; Proc. Natl. Acad. Sci.; 2001; v. 98; pp. 8850-8855.

(Continued)

*Primary Examiner* — Elizabeth C Kemmerer
*Assistant Examiner* — Kimberly A Ballard
(74) *Attorney, Agent, or Firm* — Faegre Baker Daniels LLP

(57) ABSTRACT

The present invention concerns methods and compositions of use for treatment of Alzheimer's Disease (AD). In certain embodiments, the methods concern preparation of phage-display single chain antibody libraries and screening against amyloid-beta (Aβ) protein or peptide. Anti-Aβ antibodies are selected and sequenced. In certain embodiments, synthetic Aβ binding peptides are designed and prepared, using portions of the anti-Aβ antibody sequences. The antibodies and peptides are of use for treatment of AD or for treatment of individuals at risk of developing AD. Compositions comprising anti-Aβ antibodies or Aβ binding peptides are also disclosed.

12 Claims, 6 Drawing Sheets

OTHER PUBLICATIONS

Demeester et al.; Comparison of the aggregation properties, secondary structure and apoptotoc effects of wild-type, Flemish and Dutch N-terminally truncated amyloid β peptides; Eur. J. Neurosci.; 2001; v. 13; pp. 2015-2024.

Dodart et al.; Immunization reverses memory deficits without reducing Aβ burden in Alzheimer's disease model; Nat. Neurosci.; 2002; v. 5, No. 5; pp. 452-457.

Dong et al.; Single chain Fv antibodies against neural cell adhesion molecule L1 trigger L1 functions in cultured neurons; Mol. Cell. Neurosci.; 2003; v. 22; pp. 234-247.

Fassbender et al.; Simvastatin strongly reduces levels of Alzheimer's disease β-amyloid peptides Aβ42 and Aβ40 in vitro and in vivo. Proc Natl Acad Sci; 2001; v. 98; pp. 5856-5861.

Feliche et al.; Inhibition of Alzheimer's disease β-amyloid aggregation, neurotoxicity, and in vivo deposition by nitrophenols: implications for Alzheimer's therapy; FASEB J.; 2001; v. 15; pp. 1297-1299.

Frenkel et al.; N-terminal EFRH sequence of Alzheimer's β-amyloid peptide represents the epitope of its anti-aggregating antibodies; J Neuroimmunol; 1998; v. 88; pp. 85-90.

Frenkel et al.; Immunization against Alzheimer's β-amyloid plaques via EFRH phage administration; Proc Natl Acad Sci; 2000; v. 97; pp. 11455-11459.

Frenkel et al.; Filamentous phage as vector-mediated antibody delivery to the brain; Proc. Natl. Acad. Sci.; 2002; v. 99; pp. 5675-5679.

Furlan et al.; Vaccination with amyloid-β peptide induces autoimmune encephalomyelitis in C57/BL6 mice; Brain; 2003; v. 126; pp. 285-291.

García et al.; Strategies for Neuroprotection Against L-Trans-2,4-Pyrrolidine Dicarboxylate-Induced Neuronal Damage During Energy Impairment In Vitro; J Neurosci Res.; 2001; v. 64; pp. 418-428.

Gaskin et al.; Human Antibodies Reactive with β-amyloid Protein in Alzheimer's disease; J. Exp. Med.; 1993; v. 177; pp. 1181 1186.

Gevorkian et al.; Identification of Autoimmune Thrombocytopenic Purpura-Related Epitopes Using Phage-Display Peptide Library; Clin. Immunol. Immunopathol.; 1998; v. 86; pp. 305-309.

Gevorkian et al.; Identification of Mimotopes of Platelet Autoantigens Associated with Autoimmune Thrombocytopenic Purpura; J. Autoimm.; 2000; v. 15; pp. 33-40.

Gevorkian et al.; Solid-phase synthesis of a peptide comprising the 605-611 disulfide loop of GP41, transmembrane glycoprotein of Human Immunodeficiency Virus Type 1 (HIV-1); Org Prep Proc Int; 1995; v. 27, No. 3; pp. 375-377.

Gouras et al.; Intraneuronal Aβ42 Accumulation in Human Brain; Am. J. Pathol.; 2000; v. 156; pp. 15-20.

Gyure et al.; Intraneuronal Aβ-Amyloid Precedes Development of Amyloid Plaques in Down Syndrome; Arch. Pathol. Lab. Med.; 2001; v. 125; pp. 489-492.

Hock et al.; Antibodies against β-Amyoid Slow Cognitive Decline in Alzheimer's Disease; 2003; Neuron; v. 3; pp. 547-554.

Janus et al.; Aβ peptide immunization reduces behavioural impairment and plaques in a model of Alzheimer's disease; 2000; Nature; v. 408; pp. 979-982.

Klein et al.; Targeting small Aβ oligomers: the solution to an Alzheimer's disease conundrum?; Trends in Neurosciences; 2001; v. 24, No. 4; pp. 219-224.

Kotilinek et al.; Reversible Memory Loss in a Mouse Transgenic Model of Alzheimer's Disease; 2002; J. Neurosci.; v. 22; pp. 6331-6335.

Lecerf et al.; Human single-chain Fv intrabodies counteract in situ huntingtin aggregation in cellular models of Huntington's disease; Proc. Natl. Acad. Sci.; 2001; USA; v. 98, No. 8; pp. 4764-4769.

Lemere et al.; Evidence for peripheral clearance of cerebral Aβ protein following chronic, active Aβ immunization in PSAPP mice; Neurobiol. Dis.; 2003; v. 14; pp. 10-18.

Lue et al.; Modeling Alzheimer's Disease Immune Therapy Mechanisms: Interactions of Human Postmortem Microglia With Antibody-Opsonized Amyloid-Beta Peptide; J. Neurosci. Res.; 2002; v. 70; pp. 599-610.

Ma et al.; Stabilities and conformations of Alzheimer's β-amyloid peptide oligomers (Aβ16-22, Aβ16-35, and Aβ10-35): Sequence effects; Proc. Natl. Acad. Sci.; 2002; v. 99, No. 22; pp. 14126-14131.

Manoutcharian et al.; Characterization of Cerebrospinal Fluid Antibody Specificities in Neurocysticercosis Using Phage Display Peptide Library; Clin Immunol; 1999; v. 91, No. 1; pp. 117-121.

Manoutcharian et al.; Amyloid-beta peptide specific single chain Fv antibodies isolated from an immune phage display library; J. Neuroimmunol.; 2003; v. 145; pp. 12-17.

Manoutcharian et al.; Human single Chain Fv antibodies and a complementarity determining region-derived peptide binding to amyloid-beta 1-42; Neurobiol. Dis.; 2004; v. 17; pp. 114-121.

Manoutcharian et al.; Phage-displayed T Cell Epitope Grafted into Immunoglobulin Heavy-Chain Complementarity-Determining Regions: an Effective Vaccine Design Tested in Murine Cisticercosis; Infection and Immunity; 1999; v. 67, No. 9; pp. 4764-4770.

Massieu et al.; Acetoacetate protects hippocampal neurons against glutamate-mediated neuronal damage during glycolysis inhibition; Neuroscience; 2003; v. 120; pp. 365-378.

Miller et al.; Humoral Immune Response to Fibrillar β-amyloid Peptide. Biochemistry; 2003; v. 42; pp. 11682-11692.

Mohajer, et al.; Passive Immunization against β-Amyloid Peptide Protects Central Nervous System (CNS) Neurons from Increased Vulnerability Associated with an Alzheimer's Disease-causing Mutation; J. Biol. Chem.; 2002; v. 277, No. 36; pp. 33012-33017.

Morgan et al.; Aβ peptide vaccination prevents memory loss in an animal model of Alzheimer's disease; Nature; 2000; v. 408; pp. 982-985.

Munch et al.; Potential neurotoxic inflammatory responses to Aβ vaccination in humans; J. Neural Transm.; 2002; v. 109; pp. 1081-1087.

Pfeifer et al.; Cerebral Hemorrhage After Passive Anti-Aβ Immunotherapy; Science; 2002; v. 298; p. 1379.

Pike et al.; Amino-terminal Deletions Enhance Aggregation of β-Amyloid Peptides in vitro; J. Biol. Chem.; 1995; v. 270, No. 41; pp. 23895 23898.

Pike et al.; b-Amyloid Neurotoxicity in Vitro: Evidence of Oxidative Stress but Not Protection by Antioxidants; J. Neurochem.; 1997; v. 69; pp. 1601-1611.

Poul et al.; Selection of Tumor-Specific Internalizing Human Antibodies from Phage Libraries; J. Mol. Biol.; 2000; v. 301; pp. 1149-1161.

Schenk et al.; Immunization with amyloid-β attenuates Alzheimer-disease-like pathology in the PDAPP mouse; Nature; 1999; v. 400; pp. 173 177.

Selkoe, D. J.; Alzheimer's Disease: Genes, Proteins, and Therapy; Physiological Rev.; 2001; v. 81, No. 2; pp. 741-766.

Sergeant et al.; Truncated beta-amyloid peptide species in pre-clinical Alzheimer's disease as new targets for the vaccination approach; J. Neurochem.; 2003; v. 85; pp. 1581-1591.

Zinger et al.; Peptides based on the complementarity-determining regions of a pathogenic autoantibody mitigate lupus manifestations of (NZB × NZW)F1 mice via active suppression; Int'l Immun; vol. 15, No. 2; pp. 205-214.

Ueda et al.; Amyloid β Protein Potentiates Ca2+ Influx Through L-Type Voltage-Sensitive Ca2+Channels: A Possible Involvement of Free Radicals; J. of Neurochem,; 1997; v. 68; pp. 265-271.

Sturchler-Pierrat et al.; Two amyloid precursor protein transgenic mouse models with Alzheimer disease-like pathology; Proc. Natl. Acad. Sci.; 1997; v. 94; pp. 13287-13292.

Solomon et al.; Monoclonal antibodies inhibit in vitro fribrillar aggregation of the Alzheimer β-amyloid peptide; Proc. Natl. Acad. Sci.; 1996; v. 93; pp. 452-455.

Solomon et al.; Disaggregation of Alzheimer β-amyloid by site-directed mAb; Proc. Natl. Acad. Sci.; 1997; v. 94; pp. 4109-4112.

Pogue et al.; Amino-terminal alteration of the HLA-A*0201-restricted human immunodeficiency virus pol peptide increases complex stability and in vitro immunogencity, Proc. Natl. Acad. Sci. USA, 1995, vol. 97, pp. 8166-8170.

Sarobe et al.; Enhanced in vitro potency and in vivo immunogenicity of a CTL epitope from hepatitis C virus core protein following amino acid replacement at secondary HLA-A2.1 binding positions, J. Clin. Invest, 1998, vol. 102, No. 6, pp. 1239-1248.

Lipford et al.; Peptide engineering allows cytotoxic T-cell vaccination against human papilloma virus tumour antigen, E6, Immunology, 1995, 84:298-303.

Woodberry et al.; Immunogenicity of a Human Immunodeficiency Virus (HIV) Polytope Vaccine Containing Multiple HLA A2 HIV CD81 Cytotoxic T-Cell Epitopes, Journal of Virology, Jul. 1999, vol. 73, No. 7, pp. 5320-5325.

Lipford et al.; In vivo CTL induction with point-substituted ovalbumin peptides: immunogenicity correlates with peptide-induced MHC class I stability, Vaccine, 1995, vol. 13, No. 3, pp. 313-320.

Carlos et al.; Immunogenicity of a vaccine preparation representing the variable regions of the HIV type I envelope glycoprotein, AIDS Research and Human Retroviruses, 2000, vol. 16, No. 2, pp. 153-161.

Clark et al.; Bacterial viruses as human vaccines?, Expert Rev. Vaccines, 2004 3(4):463-476.

International Search Report and Written Opinion for PCT/US2006/009751 dated Apr. 3, 2007.

* cited by examiner

COMPOSITIONS AND METHODS FOR ALZHEIMER'S DISEASE

RELATED APPLICATIONS

This application is a divisional application of U.S. patent application Ser. No. 11/773,349, filed Jul. 3, 2007, which is a divisional application of U.S. patent application Ser. No. 10/902,546, filed Jul. 29, 2004 which is a continuation-in-part of U.S. patent application Ser. No. 10/895,224, filed Jul. 20, 2004, entitled "Compositions and Methods for Alzheimer's Disease," now abandon. These applications are incorporated herein by reference in their entirety for all purposes.

GOVERNMENT RIGHTS

This invention was supported, in part, by grant AG20227 from the National Institutes of Health, (National Institute of Aging). The United States government may have certain rights in the invention.

BACKGROUND

1. Field of Invention

The present invention concerns methods and compositions of use for the treatment of Alzheimer's disease (AD) in subjects, particularly in human subjects. In certain embodiments, the methods may comprise exposure of phage-displayed human antibodies, such as single-chain Fv (scFv) antibodies, to a human amyloid-beta (Aβ42) peptide and selection of anti-Aβ42 antibodies. In other embodiments, the compositions may comprise anti-Aβ42 antibodies, for example that have been prepared by the disclosed methods. In still other embodiments, the compositions may comprise one or more synthetic peptides, peptide mimetics and/or peptide analogs containing one or more amino acid sequences selected from one or more anti-Aβ42 antibodies. Methods of therapeutic treatment of a subject may comprise administration of anti-Aβ42 peptides, peptide analogs and/or peptide mimetics containing one or more amino acid sequences selected from one or more anti-Aβ42 antibodies to a subject with AD or a subject at risk of developing AD.

2. Description of Related Art

The accumulation of amyloid-beta (Aβ) peptide in the brain and its deposition as plaques has been hypothesized to play a central role in the neuropathology of Alzheimer's Disease (AD) (Selkoe, 2001; Thorsett and Latimer, 2000; Klein et al., 2001). Neurons in the brain produce Aβ fragments from a larger precursor molecule named amyloid precursor protein (APP). When released from the cell, Aβ fragments may accumulate in extracellular amyloid plaques. It appears that not only the well-known Aβ amyloid fibrils but much smaller soluble forms of aggregated Aβ fragments (protofibrils and small oligomers), that escape detection by methods suitable for fibrils, are involved in the pathogenesis of AD (Klein et al., 2001). This explains the poor correlation between fibrillar amyloid load and disease progression.

Aβ fragments are generated through the action of specific proteases within the cell. The most important among these enzymes are beta- and gamma-secretase. It has been proposed that small compounds that cross the blood-brain barrier (BBB) and decrease but do not eliminate either beta- or gamma-secretase activity may be of use for therapies in the early clinical phases of AD. But interfering with normal metabolic reactions of the organism, such as the action of beta- and gamma-secretase, is not desirable, and an alternative approach that targets a specific pathological event, Aβ deposition, would be more appropriate for effective treatment and prevention of AD.

There are previous reports of efforts to find compounds that selectively destroy Aβ plaques. Thus, it was reported that nitrophenols inhibited the aggregation of Aβ in vitro and caused disaggregation of previously formed amyloid fibrils (Feliche et al., 2001). Also, nitrophenols protected rat hippocampal neurons in culture from the neurotoxic effect of Aβ and inhibited the formation of Aβ deposits in rat hippocampi in an in vivo model system of cerebral amyloid deposits (Feliche et al., 2001). Fassbender et al. (2001) showed that the cholesterol-lowering drugs, simvastatin and lovastatin, reduce intracellular and extracellular levels of Aβ in primary cultures of hippocampal neurons and mixed cortical neurons, and that guinea pigs treated with high doses of simvastatin showed a strong and reversible reduction of cerebral Aβ. None of these compounds to date has provided an effective treatment or cure for human AD.

Alzheimer-type neuropathology has been observed in transgenic mice in which transgenes for human APP provided elevated brain levels of Aβ. Experiments using this mouse model of AD (PDAPP transgenic mouse model) have been used to investigate many questions related to Aβ and AD. Thus, it has been shown that immunization of PDAPP mice with Aβ peptide significantly reduced amyloid deposition and certain AD-like neuropathological features in old mice, and also essentially prevented amyloid formation, neuritic dystrophy and astrogliosis in young animals (Schenk et al., 1999; Janus et al., 2000; Morgan et al, 2000).

These results suggested that the immunization with Aβ may be effective in preventing and treating AD. Janus and collaborators showed that Aβ immunization reduced both deposition of cerebral fibrillar Aβ and cognitive dysfunction in the TgCRND8 murine model of AD (a mutant, K670N/M671L and V717F, human βAPP$_{695}$ transgene expressed under the regulation of the Syrian hamster prion promoter on a C3H/B6 strain background) (Janus et al., 2000). Another study on Aβ immunization was performed by Morgan et al (2000). Those authors demonstrated that vaccination of transgenic mice with Aβ protected them from the learning and age-related memory deficits that normally occur in this mouse model of AD. The Aβ-vaccinated mice also exhibited a partial reduction in amyloid burden at the end of the study. These cumulative data suggest the use of Aβ immunization as a therapeutic approach that may prevent and, possibly, treat AD. However, in human clinical trials with Aβ42 immunization, some patients developed symptoms of brain inflammation and the phase 2A clinical trial was halted (Munch and Robinson, 2002). More recent results suggest that patients who developed significant antibody titers against Aβ42 did not demonstrate cognitive decline (Hock et al., 2003).

In the studies mentioned above a whole Aβ peptide incubated overnight in buffer was used for immunization of mice. Such Aβ solutions typically contain amyloid fibrils together with a mixture of smaller aggregates. Because of the low immunogenicity of the Aβ fibrils, repeated antigen administrations were required to obtain high levels of anti-Aβ antibodies. Moreover, immunizing with toxic fibrils may induce more accumulation of the toxic amyloid itself (Morgan et al., 2000).

Attempts to design other immunogens capable of inducing anti-Aβ antibodies with anti-aggregating properties were made. The first step in these studies was the identification of epitopes within the whole Aβ molecule to which anti-Aβ antibodies bind. Both classical synthetic peptide and phage display peptide library approaches have been applied. Thus, using a phage display peptide library it was shown that residues EFRH located at positions 3-6 of the N-terminal Aβ peptide comprised the epitope that was found to be the main regulatory site for fibril formation (Frenkel et al. 1998). Subsequently, filamentous phages displaying EFRH peptide were used as a specific and non-toxic immunogen in guinea pigs for the production of anti-aggregating antibodies (Frenkel et al., 2000). Those authors have shown that serum antibodies raised against EFRH phage prevented the Aβ neurotoxic effect and disaggregated Aβ fibrils.

One of the disadvantages of any active immunization procedure is the generation of very robust immune responses, particularly cellular immune response, that may not be desirable in an elderly patient population suffering from AD. The hypothesis that passive antibody immunotherapy could be more appropriate for these individuals promoted efforts towards the generation of antibody reagents that are capable of preventing and clearing amyloid aggregates. Monoclonal antibodies raised against Aβ fragments spanning amino acid residues 1-28, prevented the aggregation of Aβ and disaggregated Aβ fibrils in vitro (Solomon et al., 1996; Solomon et al. 1997). Splenocytes from actively immunized mice demonstrated a T-cell proliferative response to Aβ in vitro, indicating the possible involvement of T-cell immunity in the therapeutic effect of immunization.

It has been determined that peripherally administered polyclonal and monoclonal antibodies against Aβ as well as their Fab or scFv regions entered the central nervous system (CNS) and reduced plaque burden along with reduction of pathology in a mouse model for AD (Bard et al., 2000; Frenkel et al., 2000; Bacskai et al., 2002; Kotilinek et al., 2002). Those results indicate that in the absence of T-cell immunity, antibodies or their fragments are sufficient to decrease amyloid deposition and AD-like pathology via classical Fc-dependent phagocytosis or direct disruption of both soluble assemblies (Kotilinek et al., 2002) or fibrils of Aβ peptide. In addition, the reduction of brain Aβ burden by peripheral administration of the anti-Aβ monoclonal antibody m266, that was capable of facilitating the clearance of Aβ out of the CNS to plasma, has been reported (DeMattos et al., 2001).

However, in another study passive immunization also demonstrated adverse side effects, such as microhemorrhages, after passive administration of mouse monoclonal anti-amino terminal Aβ antibody in APP23 transgenic mice (Pfeifer et al., 2002). This mouse model exhibits the age-related development of amyloid plaques and neurodegeneration as well as cerebral amyloid angiopathy (CAA) similar to that observed in the human AD brain (Sturchler-Pierrat et al., 1997; Calhoun et al., 1999). A possible link may exist between adverse side effects noted in APP23 transgenic mice and neuroinflammatory complications of immunization seen in a human trial. Thus, a need exists for an AD therapy that would be effective to inhibit or reverse formation of Aβ fibrils in the brain, while exhibiting reduced side effects compared to presently available immunotherapies.

BRIEF DESCRIPTION OF THE DRAWINGS

The following drawings form part of the present specification and are included to further illustrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

Figure 1:
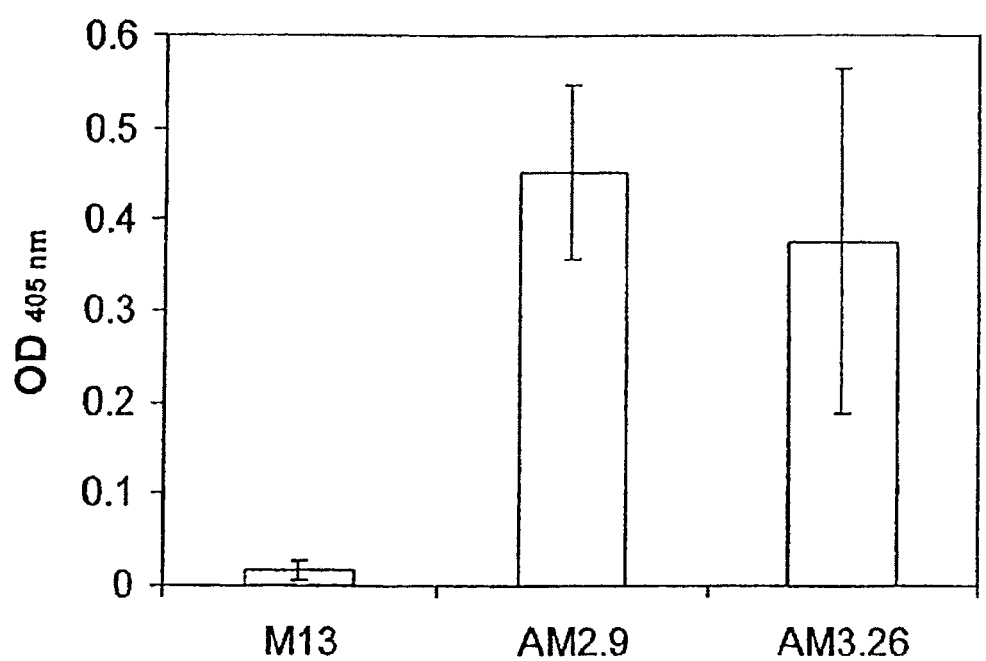
FIG. 1. ELISA binding of Aβ42 with selected scFv antibody bearing phage. Phage clones were added to the Aβ42-coated wells. Bound phage was detected using HRP-conjugated anti-M13 monoclonal antibody. Wild-type phage was used as a negative control. Mouse anti-Aβ42 serum was used as a positive control and showed $OD_{405}$=2.29±0.022.

As used herein, "a" or "an" may mean one or more than one of an item.

As used herein, a "subject" refers generally to a mammal. In certain embodiments, the subject is a human.

As used herein, "about" means plus or minus ten percent. For example, "about 100" would refer to a number between 90 and 110.

As used herein, "ameliorate" means to decrease the severity of symptoms of a disease or condition; to make better or become better; to improve. The skilled artisan will realize that a method of treatment and/or the administration of a composition may act beneficially to ameliorate the symptoms of a disease or condition, without eliminating or curing the disease or condition. In some cases, the method and/or administration may act to delay the onset of the disease or condition, and/or reduce the probability of the disease or condition occurring, and/or may delay or diminish the progression of the disease or condition from a milder form to a more severe form.

Generation of Anti-Aβ Binding Peptides for Treatment of AD in Humans

It was nearly 100 years ago when Behring and Kitasato first reported the passive immunotherapy technique, and 25 years ago when Kohler and Milstein developed hybridoma technology for monoclonal antibody production. However, until very recently, there have been few antibody-based products available for immunotherapy. This delay may be, in part, explained by the fact that mouse antibodies trigger a human anti-mouse antibody response. Chimeric and humanized recombinant antibodies have been constructed and are in clinical trials.

Since the pathological effects of Aβ are confined only to the central nervous system (CNS), there is another requirement for antibodies to be used for AD therapy. It is necessary to overcome the low permeability of the blood-brain barrier (BBB) and target anti-aggregating antibodies to the Aβ aggregates in brain. Antibody engineering methods may be applied to minimize the size of antibodies while maintaining their specific function. Currently, the most frequently used fragments of antibodies are the Fab fragments made by the association of the whole light chain and the Fd chain of the immunoglobulin molecule; and single-chain Fv (scFv) fragment which is obtained by association of the variable domains of the heavy chain and the light chain of the immunoglobulin molecule and a flexible peptide linker of 15-20 residues.

In the last decade, antibody phage display and bacterial expression systems gave rise to many recombinant antibodies demonstrating therapeutic properties in various disease models. It has been shown that phage may be used as gene delivery vehicles. Thus, inhibition of murine leukaemia virus retrotranscription by the intracellular expression of a phage-derived anti-reverse transcriptase antibody fragment has been shown (Gargano and Cattaneo, 1997). Frenkel et al (2000) applied the phage display antibody fragment approach to AD studies. They constructed a single-chain antibody from variable regions of heavy and light chain genes of the parental anti-Aβ IgM monoclonal antibody (Frenkel et al. 2000). By introducing mutations into the original sequence, these authors engineered improved antibody variants with anti-aggregating properties similar to the parent IgM antibody but with higher affinity and increased storage stability.

Another approach for generating scFvs is the selection of a specific antibody from a large phage display antibody library. Phage display antibody libraries may be constructed from immunoglobulin genes derived from a wide variety of tissues, including peripheral blood, bone marrow and lymph nodes. These tissues are frequently obtained from immunologically naive healthy donors. These non-immune libraries have been shown to provide specific antibodies to a number of disease-related antigens. An alternative source of mRNA for the construction of phage display antibody libraries are the same tissues but from patients who have mounted an immune response to disease-related antigens. Finally, another approach may be the use of animals, generally mice, immunized with an antigen of interest, since in this case the libraries of antibodies may contain a larger pool of relevant antibodies which can be selected by panning against the given antigen. Thus, using a large naïve human scFv library, human scFv intrabodies counteracting in situ Huntington aggregation in cellular models of Huntington's disease were obtained (Lecerf et al. 2001).

For AD, anti-Aβ scFv antibodies are of interest and may be applied both extracellularly and intracellularly (intrabodies). These scFv can prevent the formation of Aβ aggregates, dissolve existing fibrils, pro-fibrils or oligomers as well as, in the case of intrabodies, may interfere with the interactions of APP with other factors that are involved in directing it into the pathological pathway. Recent studies have demonstrated intraneuronal accumulation and immunoreactivity of Aβ42 and the presence of stable dimers of Aβ42 in neural cells in culture, before their release into the medium (Selkoe, 2001; Gouras et al., 2000). These observations emphasize the potential therapeutic effect of internalizing antibodies for prevention of intraneuronal Aβ42 aggregation for the treatment of AD. The therapeutic potential of intrabodies was demonstrated previously for tumor-specific antibodies (Poul et al. 2000).

Existing data pointing to a possibility to interfere with AD by interfering with Aβ aggregation. Phage display generated antibody fragments may be selected that are capable of penetrating the BBB and targeting Aβ aggregates via extracellular or intracellular approaches. In one embodiment, the phage display antibody library may be constructed using cDNA synthesized from mRNA purified from lymph nodes of mice immunized with Aβ peptide. The main advantage of this approach would be the presence in the constructed library of anti-Aβ antibodies with all possible specificities induced by Aβ immunization. In a previously published study antibodies to a limited number of epitopes were evaluated (Manoutcharian et al., 2003, J. Neuroimmunol. 145:12-17). The library of anti-Aβ scFvs may be affinity selected against biotinylated Aβ peptide, and the selected phage clones expressing specific scFvs evaluated by in vitro Thioflavin T binding assay for selection of those clones that possess anti-aggregating properties.

The selected molecules may be tested for their ability to inhibit Aβ neurotoxicity in vitro. The amino acid sequences of the inserts of the most positive clones may be determined and synthetic peptides with sequences of antibody complementarity-determining regions (CDRs) may be prepared and used as "mini-antibodies". An immunological anti-aggregation approach is a powerful tool for further evaluation of the neuropathological events and for therapeutic interference in AD, and is of use to derive molecules with anti-aggregating properties in vivo.

Efforts have been made to further screen antibodies recognizing other linear or conformational epitopes within Aβ that may be biologically functional without being associated with the development of adverse events. This could be achieved, for example, by using phage-displayed recombinant antibody fragment (Fab or scFv) libraries that result in the generation of a panel of specific antibodies quickly, easily and inexpensively in vitro. In a previously published study (Manoutcharian et al., 2003) we reported two Aβ42-specific scFv antibodies selected from an immune mouse anti-Aβ42 scFv phage display library.

However, all previous studies including that of our group on anti-Aβ antibodies or their fragments utilized murine antibodies that could present an obstacle when progressing to human trials. In the present disclosure we selected and characterized two new anti-Aβ phage-displayed scFv antibodies using a non-immune human scFv antibody library. We also synthesized a peptide based on the sequence of Ig heavy chain ($V_H$) complementarity-determining region (CDR3) of the most positive scFv-expressing phage clone and characterized its binding to Aβ42 by ELISA. We demonstrated that CDR3-based peptide exhibited the same recognition pattern as the parent antibody fragment. In addition, we demonstrated for the first time that a CDR3-based peptide had neuroprotective potential against Aβ42 mediated neurotoxicity in hippocampal cultured neurons. Our results show that not only scFvs recognizing Aβ42 but also synthetic peptides based on $V_H$ CDR3 sequences of these antibodies are novel candidates for small molecule-based therapy against AD.

Phage Display

Various methods of phage display and methods for producing diverse populations of peptides are well known in the art. For example, U.S. Pat. Nos. 5,223,409; 5,622,699 and 6,068,829, the Examples section of each of which is incorporated herein by reference, disclose methods for preparing a phage library. The phage display technique involves genetically manipulating bacteriophage so that small peptides can be expressed on their surface (Smith et al., 1985, 1993).

The potential range of applications for this technique is quite broad, and the recent past has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions. This method has also been used to identify novel peptide ligands that serve as leads to the development of peptidomimetic drugs or imaging agents (Arap et al., 1998). In addition to peptides, larger protein domains such as single-chain antibodies can also be displayed on the surface of phage particles (Arap et al., 1998).

In various embodiments, a phage display library prepared from cDNAs obtained from expressed antibody-encoding mRNA may be prepared as discussed in the Examples and screened in vitro against Aβ protein or peptide. One or more rounds of screening may be performed until a population of selective binders is obtained. The amino acid sequence of the peptides is determined by sequencing the DNA corresponding to the peptide insert in the phage genome. The identified anti-Aβ peptide can then be produced as a synthetic peptide by standard protein chemistry techniques (Smith et al., 1985).

Proteins and Peptides

In certain embodiments, the present invention concerns novel compositions comprising at least one protein or peptide. As used herein, a protein or peptide generally refers, but is not limited to, a protein of greater than about 200 amino acid; a polypeptide of greater than about 100 amino acids; and/or a peptide of from about 3 to about 100 amino acids. For convenience, the terms "protein," "polypeptide" and "peptide are used interchangeably herein.

In certain embodiments the size of the protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 3 below.

TABLE 3

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3- Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | Meile | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, or the chemical synthesis of proteins or peptides. Alternatively, various commercial preparations of proteins, polypeptides and peptides are known to those of skill in the art and proteins or peptides of specific sequence may be obtained from a variety of commercial vendors known in the art (e.g., Midland Certified Reagents, Midland, Tex.). Peptides containing derivatized amino acid residues may be prepared by incorporating such residues into the peptide chain during synthesis. Alternatively, modified amino acid residues may be prepared by chemical derivatization after peptide synthesis, for example using side-chain specific chemical modifying agents well known in the art.

Peptide Mimetics

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the anti-Aβ binding peptides disclosed herein, but with altered and even improved characteristics.

Fusion Proteins

In certain embodiments, the present invention may concern fusion proteins. These molecules may have all or a substantial portion of an anti-Aβ binding peptide, linked at the N- or C-terminus, to all or a portion of a second polypeptide or protein. For example, fusions may employ leader sequences from other species to permit the recombinant expression of a protein in a heterologous host. Inclusion of a cleavage site at or near the fusion junction may be used to facilitate removal of the extraneous polypeptide after purification. In other cases, a leader sequence may be included to facilitate intracellular targeting of an anti-Aβ binding peptide. Other useful fusions may include linking of functional domains, such as active sites from enzymes or transmembrane regions. These examples are not meant to be limiting and it is contemplated that within the scope of the present invention virtually any protein or peptide could be incorporated into a fusion protein comprising an anti-Aβ binding peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the anti-Aβ binding peptide to a DNA sequence encoding the second peptide or protein, followed by expression of the intact fusion protein.

Protein Purification

Certain embodiments may concern isolation and/or purification of a protein or peptide, such as an anti-Aβ binding peptide. Protein purification techniques are well known to those of skill in the art. The protein or peptide of interest may be purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast protein liquid chromatography (FPLC) or even HPLC. For short peptides, reverse-phase HPLC may be of use.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind to. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. For example, Aβ42 peptide could be used to affinity purify antibodies, antibody fragments or peptides.

Synthetic Peptides

Because of their relatively small size, the anti-Aβ binding peptides of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979). Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

Antibodies

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988). In preferred embodiments, monoclonal antibodies are used. Antibodies against a wide variety of antigens are available from commercial sources. Alternatively, antibodies against a novel target may be prepared as disclosed herein.

Antibodies may be prepared using conventional immunization techniques, generally known in the art. A composition containing antigenic epitopes can be used to immunize one or more experimental animals, such as a mouse, which will then produce specific antibodies against the antigens of interest.

As is well known in the art, a given composition may vary in its immunogenicity. It is often necessary to boost the host immune system, as may be achieved by coupling a peptide or polypeptide immunogen to a carrier. Exemplary carriers are keyhole limpet hemocyanin (KLH) and bovine serum albumin (BSA). Other albumins such as ovalbumin or mouse serum albumin also can be used as carriers. Techniques for conjugating a polypeptide to a carrier protein are well known in the art and include use of cross-linking reagents such as glutaraldehyde, m-maleimidobenzoyl-N-hydroxysuccinimide ester, carbodiimide and bis-biazotized benzidine. The immunogenicity of a particular immunogen composition may also be enhanced by the use of non-specific stimulators of the immune response, known as adjuvants. Exemplary adjuvants include complete Freund's adjuvant (a non-specific stimulator of the immune response containing killed *Mycobacterium tuberculosis*), incomplete Freund's adjuvant and aluminum hydroxide adjuvant.

A variety of routes can be used to administer the immunogen (subcutaneous, intramuscular, intradermal, intravenous and intraperitoneal). Booster injections also may be given. The process of boosting and tittering is repeated until a suitable titer is achieved. When a desired level of immunogenicity is obtained, the immunized animal can be bled and the serum isolated and stored, and/or the animal can be used to generate monoclonal antibodies.

Monoclonal antibodies may be readily prepared through use of well-known techniques, such as those exemplified in U.S. Pat. No. 4,196,26. Typically, this involves immunizing a suitable animal with a selected immunogen composition. Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes. In various embodiments where mRNAs encoding antibody proteins are of use, the mRNAs to be used may potentially be obtained from the spleens or other tissues of immunized animals.

The techniques described above are exemplary only. Immunization techniques generally known in the art and summarized above may be of use to increase the fraction of anti-Aβ antibodies expressed by a host, prior to preparation of phage-display libraries from the antibody encoding mRNAs of the immunized host. As disclosed in the following Examples, mRNA fractions encoding antibodies against Aβ protein or peptide may be purified, converted to cDNAs and amplified using standard kit technologies. Such antibodies or anti-body fragments may be prepared following immunization of a subject with the target protein or peptide of interest or may alternatively be prepared from naïve subjects.

Imaging Agents and Radioisotopes

In certain embodiments, the claimed peptides or proteins of the present invention may be attached to imaging agents of use for imaging and diagnosis of various diseased organs or tissues, such as brain. Many appropriate imaging agents are known in the art, as are methods for their attachment to proteins or peptides (see, e.g., U.S. Pat. Nos. 5,021,236 and 4,472,509). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptides are diethylenetriaminepentaacetic acid (DTPA) and ethylene diaminetetraacetic acid (EDTA). Also contemplated for use are fluorescent labels, including rhodamine, fluorescein isothiocyanate and renographin.

In certain embodiments, the claimed anti-Aβ binding peptides may be linked to a secondary binding ligand or to an enzyme (an enzyme tag) that will generate a colored product upon contact with a chromogenic substrate. For example, the binding peptides may be of use for histologic examination of tissue samples for the presence of Aβ fibrils. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241.

Nucleic Acids

Nucleic acids of use may encode an anti-Aβ binding peptide. The nucleic acid may be derived from complementary DNA (cDNA) or synthetic DNA. A "nucleic acid" as used herein includes single-stranded and double-stranded molecules, as well as DNA, RNA, chemically modified nucleic acids and nucleic acid analogs. It is contemplated that a nucleic acid within the scope of the present invention may be of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 or greater nucleotide residues in length.

It is contemplated that anti-Aβ binding peptides may be encoded by any nucleic acid sequence that encodes the appropriate amino acid sequence. The design and production of nucleic acids encoding a desired amino acid sequence is well known to those of skill in the art, using standardized codon tables (see Table 4 below). In preferred embodiments, the codons selected for encoding each amino acid may be modified to optimize expression of the nucleic acid in the host cell of interest. Codon preferences for various species of host cell are well known in the art.

TABLE 4

| Amino Acid | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In addition to nucleic acids encoding the desired anti-Aβ binding peptides, the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

Expression of Proteins or Peptides

In certain embodiments, it may be desirable to make and use an expression vector that encodes and expresses a particular anti-Aβ binding peptide. For relatively short anti-Aβ binding peptides, it is within the skill in the art to design synthetic DNA sequences encoding a specified amino acid sequence, using a standard codon table. Genes may be optimized for expression in a particular species of host cell by utilizing well-known codon frequency tables for the desired species. Genes may represent genomic DNA sequences, containing both introns and exons, or more preferably comprise cDNA sequences, without introns.

Regardless of the source, a gene of interest can be inserted into an appropriate expression system. The gene can be expressed in any number of different recombinant DNA expression systems to generate large amounts of the polypeptide product, which can then be purified and used in various embodiments of the present invention.

Examples of expression systems known to the skilled practitioner in the art include bacteria such as *E. coli*, yeast such as *Pichia pastoris*, baculovirus, and mammalian expression systems such as in Cos or CHO cells. Expression is not limited to single cells, but may also include peptide production in genetically engineered transgenic animals, such as rats, cows or goats. A complete gene can be expressed or, alternatively, fragments of the gene encoding portions of polypeptide can be produced.

The gene or gene fragment encoding a polypeptide may be inserted into an expression vector by standard subcloning techniques. An *E. coli* expression vector may be used which produces the recombinant peptide as a fusion peptide, allowing rapid affinity purification of the protein. Examples of such fusion peptide expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the activity or binding properties of the recombinant peptide. For example, both the FLAG system and the 6xHis system add only short sequences. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant protein. See Summers et al., A Manual of Methods for Baculovirus Vectors and Insect Cell Culture Procedures, Texas Agricultural Experimental Station; U.S. Pat. No. 4,215,051.

As an alternative to recombinant polypeptides, synthetic peptides corresponding to short peptides of interest may be prepared. Such peptides are at least six amino acid residues long, and may contain up to approximately 35-50 residues, and may be synthesized using automated peptide synthesis machines, such as those available from Applied Biosystems (Foster City, Calif.).

Substitutional variants typically contain an alternative amino acid at one or more sites within the protein, and may be designed to modulate one or more properties of the polypeptide such as stability against proteolytic cleavage. Substitutions preferably are conservative, that is, one amino acid is replaced with one of similar size and charge. Conservative substitutions are well known in the art and include, for example, the changes of: arginine to lysine; asparagine to glutamine or histidine; aspartate to glutamate; cysteine to serine; glutamine to asparagine; glutamate to aspartate; histidine to asparagine or glutamine; isoleucine to leucine or valine; leucine to valine or isoleucine; lysine to arginine, glutamine, or asparagine; methionine to leucine or isoleucine; phenylalanine to tyrosine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises an isolated nucleic acid encoding a peptide of interest under the control of, or operatively linked to, one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant peptide.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant bacteriophage DNA, plasmid DNA or cosmid DNA expression vectors.

Certain examples of prokaryotic hosts are E. coli strain RR1, E. coli LE392, E. coli B, E. coli X 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is often transformed using pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as E. coli LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographa californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

Formulations and Routes for Administration to Patients

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Labels

In certain embodiments of the invention, one or more labels may be attached to a binding moiety, probe, primer or other molecule. A number of different labels may be used, such as fluorophores, chromophores, radioisotopes, enzymatic tags, antibodies, bioluminescent, electroluminescent, phosphorescent, affinity labels, nanoparticles, metal nanoparticles, gold nanoparticles, silver nanoparticles, magnetic particles, spin labels or any other type of label known in the art.

Non-limiting examples of affinity labels include an antibody, an antibody fragment, a receptor protein, a hormone, biotin, DNP, and any polypeptide/protein molecule that binds to an affinity label.

Non-limiting examples of enzymatic tags include urease, alkaline phosphatase or peroxidase. Colorimetric indicator substrates can be employed with such enzymes to provide a detection means visible to the human eye or spectrophotometrically.

Non-limiting examples of photo detectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. These and other luminescent labels may be obtained from commercial sources such as Molecular Probes (Eugene, Oreg.).

In other embodiments of the invention, labels of use may comprise metal nanoparticles. Methods of preparing nanoparticles are known. (See e.g., U.S. Pat. Nos. 6,054,495; 6,127,120; 6,149,868; Lee and Meisel, *J. Phys. Chem.* 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as Nanogold® nanoparticles from Nanoprobes, Inc. (Yaphank, N.Y.).

In some embodiments of the invention, proteins may be labeled using side-chain specific and/or selective reagents. Such reagents and methods are known in the art. Non-limiting exemplary reagents that may be used include acetic anhydride (lysine, cysteine, serine and tyrosine); trinitrobenzenesulfonate (lysine); carbodiimides (glutamate, aspartate); phenylglyoxal (arginine); 2,3-butanedione (arginine); pyridoxal phosphate (lysine); p-chloromercuribenzoate (cysteine); 5,5'-dithiobis(2-nitro-benzoic acid) (cysteine); dimethylpyrocarbonate (lysine, histidine); N-bromosuccinimide (tryptophan) and tetranitromethane (cysteine, tyrosine). Various methods for attaching labels to nucleic acids and/or oligonucleotides are known in the art and may be used. For example, water-soluble carbodiimides may be used to cross-link the phosphate groups of nucleic acids or oligonucleotides to various labels. Amino or sulfhydryl modified oligonucleotides or nucleic acids may be attached to labels using known bifunctional crosslinking reagents (Running et al., *BioTechniques* 8:276-277, 1990; Newton et al., *Nucleic Acids Res.* 21:1155-62, 1993).

In alternative embodiments of the invention, various cross-linking reagents known in the art, such as homo-bifunctional, hetero-bifunctional and/or photoactivatable cross-linking reagents may be used. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithio-bispropionimidate; N-succinimidyl-3-(2-pyridyldithio)propionate; 4-(bromoaminoethyl)-2-nitrophenylazide; and 4-azidoglyoxal. Such reagents may be modified to attach various types of labels, such as fluorescent labels. The skilled artisan will realize that such cross-linking reagents are not limited to use with proteins, but may also be used with other types of molecules.

Kits

In some embodiments, the present invention concerns kits for use with the methods described herein. The kits may comprise, in suitable container means, one or more anti-Aβ binding peptides and/or antibodies, a control Aβ protein or peptide (e.g., Aβ42), a control peptide that is not recognized by the anti-Aβ binding peptides and/or antibodies, and various buffers, reagents, enzymes and other standard ingredients well known in the art.

The container means of the kits will generally include at least one vial, test tube, flask, bottle, syringe or other container means, into which the probes and/or primers may be placed, and preferably, suitably aliquoted. Where an additional component is provided, the kit will also generally contain additional containers into which this component may be placed. The kits of the present invention will also typically include a means for containing the peptides or proteins and any other reagent containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Anti-Aβ Antibodies in Mice

A single-chain fragment variable (scFv) antibody library displayed on phage was constructed using spleen cells from mice immunized with human amyloid-beta peptide (Aβ42). This anti-Aβ42 scFv immune antibody library was selected against human Aβ42. A number of positive clones were obtained, and sequences of $V_H$ and $V_\kappa$ genes were analyzed using ExPASy and BLAST computer tools. This analysis revealed that only two unique clones with identical $V_H$ and $V_\kappa$ complementarity determining region (CDR) (except HCDR2) and identical germline genes were selected, indicating that oligoclonal immune response was occurring in Aβ42-immunized mice. Aβ42-specific scFv antibodies selected from this immune anti-Aβ42 phage antibody library may be of use for the development of therapeutic molecules for Alzheimer's disease (AD).

Methods

Construction of Anti-Ab scFv Antibody Phage Display Library

Spleen cells from mice immunized with Aβ42 were used as a source of immunoglobulin genes. Three 6-week-old BALB/c mice were immunized with Aβ42 (BACHEM Bioscience, King of Prussia, Pa., USA). Aβ42 was first suspended in pyrogen-free type I water at 2 mg/ml, then mixed with 10× PBS to yield 1× PBS and incubated overnight at 37° C. This immunogen preparation was mixed with Freund's complete adjuvant for priming of mice, and with incomplete Freund's adjuvant for boost injections. Four immunizations were performed at 14-day interval.

One week after the fourth immunization, mouse sera were tested in ELISA for the presence of specific anti-Aβ42 antibodies. Briefly, a 96-well plate (Nunc, Roskilde, Denmark) was coated with 1 µg/ml of Aβ42 in phosphate buffer (pH 7.8) overnight at 4° C. The plate was washed with phosphate buffer containing 0.1% Tween-20 (PBS-Tween) and blocked with PBS containing 2% bovine serum albumin (PBS-BSA). After washing, mouse sera diluted in PBS-BSA 1% was added, and the plate was incubated for 1 h at 37° C. The plate was washed and goat anti-mouse IgG conjugated with HRP (Zymed, San Francisco, Calif., USA) was added. After incubation for 1 h at 37° C., the plate was washed and 2,2'-azino-bis-(3-ethyl-benzothiazoline-6-sulphonic acid (ABTS) single solution (Zymed) was added. The OD reading at 405 was registered using Opsys MR Microplate Reader (DYNEX Technologies, Chantilly, Va., USA).

The mRNA was extracted from the splenocytes of immunized mice using QuickPrep mRNA Purification Kit (Amersham Pharmacia Biotech, USA) as recommended by the manufacturer. First, strand cDNA was synthesized from mRNA using random pd(N)6 primer according to RPAS Mouse ScFv Module (Amersham Pharmacia Biotech) manufacturer's instructions. Then Ig heavy ($V_H$) and light ($V_\kappa$) genes were amplified from cDNA using specific primers provided in the same kit. PCR products were gel purified using a Concert Rapid Gel Extraction System (Amersham Pharmacia Biotech) and used in assembly reaction to join $V_H$ and $V_\kappa$ DNA into a single chain ($V_H$-$V_\kappa$) with linker DNA.

This DNA was used as a template for PCR reamplification with flanking oligonucleotides containing appended restriction sites SfiI and NotI. The DNA of scFv gene repertoires were gel purified, digested with SfiI and NotI and ligated into the similarly digested vector pCANTAB-5E DNA (Amersham Pharmacia Biotech). After extraction with phenol/chloroform and ethanol precipitation, the ligation mix was electroporated into 50 µl *Escherichia coli* TG1 cells using Gene Pulser II System (Bio-Rad Laboratories, Hercules, Calif., USA). Ten electroporations were performed, and the resultant phagemid library was rescued/amplified using M13KO7 helper phage (Invitrogen, Carlsbad, Calif., USA) and the Expression Module/Recombinant Phage Antibody System (Amersham Pharmacia Biotech).

The transformed TG1 cells were plated on LB-Amp plates. The diversity of the library was $2.2 \times 10^5$ individual recombinants. The typical phage yields were $10^{10}$-$10^{11}$ colony-forming units (cfu) per milliliter of culture medium.

Selection of Aβ-Specific scFV Antibodies by Biopanning Against Aβ

Selection and amplification procedures for the scFv library was carried out essentially as described for peptide libraries in our previous studies (Gevorkian et al., 1998; Manoutcharian et al., 1999; Gevorkian et al., 2000), using 96-well plates (Nunc) coated overnight with 2 µg/ml of Aβ42 in PBS. Plates were blocked with PBS/BSA 2%, and then phages were added at a concentration of $10^{13}$/ml. After incubation for 4 h at 4° C., plates were washed with cold PBS-Tween, and bound phage was eluted using 100 µl/well of 100 mM Triethylamine. Tris-HCl (1 M) was added to neutralize the eluate. In each round, we rescued the phagemid library using helper phage M13K07. Three rounds of biopanning were performed.

ELISA Screening of Selected scFv Antibodies Expressed on Phage

After each round of selection, single ampicillin-resistant colonies were used to innoculate 96-well cell culture plates (Costar, Corning, N.Y., USA) containing 125 µl of 2-YTAmp-glucose. Plates were incubated for 4 h at 37° C. and 100 µl of 2×YT containing hyperphage (Rondot et al., 2001) was added to each well. After 30 min of incubation without shaking and 30 min of incubation with shaking, plates were centrifuged and supernatants were removed.

Fresh 2×YT without glucose but supplemented with ampicillin and kanamycin was added to each well, and plates were incubated overnight at 30° C. with shaking Microtiter plates (Nunc) were coated with Aβ and blocked as described above, supernatants from plates containing phage were added, and after incubation for 1 h at 37° C., plates were washed with PBS-Tween. HRP/Anti-M13 monoclonal conjugate (Amersham Pharmacia Biotech) diluted in PBS-BSA 1% was added, and plates were incubated for 1 h at 37° C. Plates were washed and ABTS single solution (Zymed) was added. The OD reading at 405 was registered using Opsys MR Microplate Reader (DYNEX Technologies). The reported data are representative of three different experiments.

DNA Sequencing

The DNA sequences of the inserts of selected scFv expressing phagemid clones were determined using automated ABI PRISM 310 Genetic Analyzer (Applied Biosystems, Foster City, Calif., USA), miniprep-purified (Qiagen)

double-stranded DNA of the clones and pCANTAB 5 Sequencing Primer Set (Amersham Pharmacia Biotech). The DNA and deduced amino acid sequences were analyzed by computer search with ExPASy Molecular Biology server, BLAST and IMGT (the International Im-MunoGeneTics) Information System database. The DNA and amino acid sequences of isolated scFvs were submitted to the GenBank database.

Results

Construction of Anti-Ab scFv Antibody Phage Display Library

Preparation of scFv antibody phage display libraries involves four stages: (1) isolation of mRNA from a source of antibody-producing cells; (2) preparation of the scFv repertoires; (3) cloning of the scFv repertoires into a phagemid vector; and (4) expression of the scFv in the surface of phage. Spleen cells from mice immunized with Aβ were used to generate a scFv phage antibody library. The $V_H$ and $V_\kappa$ genes were amplified from mRNA, spliced together and the obtained scFv gene repertoires were cloned into pCANTAB-5E to generate a phage displayed scFv antibody library of $2.2 \times 10^5$ transformants. PCR analysis of 16 randomly selected clones showed that the majority carried full length inserts (data not shown).

Selection of Ab-Specific scFV Antibodies by Biopanning Against Aβ and ELISA Screening of Selected scFvs In order to identify Aβ42-specific scFv antibodies, the constructed immune library was rescued using M13KO7 helper phage and selected against human Aβ42. Three rounds of biopanning were performed, and 180 individual clones were randomly picked, rescued using hyperphage and screened for their capacity to bind to Aβ42 in ELISA. Wild-type phage was used as negative control to discard non-specific interactions between phage and Aβ42. OD readings of binding of positive clones to Aβ42 are shown in FIG. 1. PCR analysis showed that all positive clones carried full-length DNA inserts (not shown).

Sequence Analysis of $V_H$ and $V_\kappa$ Genes of Selected scFvs

Eight phage clones with the highest OD values in ELISA were further analyzed by determining the nucleotide sequences encoding their $V_H$ and Vκ genes. The amino acid sequences of these clones were deduced from their nucleotide sequences. The obtained sequences were analyzed using ExPASy and BLAST computer tools and aligned to the most homologous germline gene sequences in the IMGT/DNA PLOT directory (Table 1).

As shown in Table 1, only two unique clones with identical $V_H$ and Vκ complementarity determining regions (CDR) (except HCDR2) and identical germline genes/segments were found. The clone AM 2.9, isolated seven times, and AM 3.26, isolated one time, have eight nucleotide (nt) and four amino acid (aa) differences in framework region 1 (FR1), HCDR2 and FR3 of $V_H$ and four nt and one aa in FR1 of Vκ chain (not shown). Extensive differences at both nt and aa level from germline sequences were found in isolated clones including four and three aa changes in CDR3 regions of both heavy and light chains (Table 1). A single UAA and UGA stop codons were present in $V_H$ FR1 and in FR3 regions of AM 2.9 and AM 3.26 clones, respectively. Most probably, these stop codons are translated on ribosomes through incorporation of tryptophan (W) into the polypeptide chain.

The sequences of the scFv antibody fragments determined as discussed above have been deposited in GenBank and are available at GenBank Accession Numbers AY307933 or AAP69671 (AM 3.26) and AY307932 or AAP69670 (AM 2.9). It will be apparent to the skilled artisan that the disclosed scFv amino acid sequences, or fragments thereof, may be of use for administering to subjects with AD or subjects at risk of developing AD to prevent the formation of amyloid plaques or to disassemble existing amyloid plaques. As discussed below, in certain embodiments such scFv sequences or fragments may be administered to a subject incorporated into a vector, for example, M13 phage. The amino acid sequences of AM 3.26 and AM 2.9 are as disclosed below.

AM 2.9

(SEQ ID NO: 5)
QVKLQESGTEVVKPGASVKLSCKASGYIFTSYDIDWVRQTPEQGLE
WIGWIFPGEGSTEFNEKFKGRATLSVDKSSTAYMELTRLTSEDSA
VYFWARGDYYRRYFDLWGQGTTVTVSSSGGGSGGGGSGGGGSDIEL
TQSPTIMSASPGERVTMTCSASSSIRYIYWYQQKPGSSPRLLIYDT
SNVAPGVPFRFSGSGSGTSYSLTINRMEAEDAATYYCQEWSGYPYT
FGGGTKLELKR

AM 3.26

(SEQ ID NO: 6)
QVKLQQWGTEVVKPGASVKLSCKASGYIFTSYDIDWVRQTPEQGLE
WIGWIFPGEGSTEYNEKFKGRATLSVDKSSTAYMELTRLTSEDSA
VYFCARGDYYRRYFDLWGQGTTVTVSSCGGGSGGGGSGGGGSDIEL
TQSPAIMSASPGERVTMTCSASSSIRYIYWYQQKPGSSPRLLIYDT
SNVAPGVPFRFSGSGSGTSYSLTINRMEAEDAATYYCQEWSGYPYT
FGGGTKLELKR

As discussed below, part or all of the mouse scFv sequences may be of use for treatment of AD or a predisposition to AD. Further, part or all of the sequence of the HCDR3 region of the scFv antibody fragments may be of particular use for therapeutic treatment of AD or pre-AD conditions. In the case of the mouse scFv fragments identified, both AM 2.9 and AM 3.26 exhibited the same HCDR3 sequence-GDYYRRYFDL (SEQ ID NO:7)

TABLE 1

Germline genes/segments and CDR3 sequences of scFv antibodies isolated from immune library selected on 13-amyloid peptide[a]

| Clone | $V_H$ germline | $D_H$ germline | $J_H$ germline | HCDR3 | $V_K$ germline | $J_L$ germline | LCDR3 |
|---|---|---|---|---|---|---|---|
| AM2.9 | IGHV1S24*01 (41)[b] | IGHD-SP2.x*01 (8)[b] | IGHJ2*01 (15)[b] | GDYYRRYFDL (4)[c] | IGKV4-55*01 (9)[b] | IGKJ5*01 (3)[b] | QEWSGYPYT (3)[c] |
| AM3.26 | IGHVIS24*01 (38)[b] | IGHD-SP2.x*01 (8)[b] | IGHJ2*01 (14)[b] | GDYYRRYFDL (4)[c] | IGKV4-55*01 (24)[b] | IGKJ5*01 (3)[b] | QEWSGYPYT (3)[c] |

[a]Mouse germline $V_H$, $V_K$, $D_H$, $J_H$ and $J_L$ segments have been assigned as detailed in the International ImMunoGeneTics Information System (IMGT). These two clones with identical $V_H$ and $V_L$ CDR3 regions showed different HCDR2 and framework regions, as indicated by their differences from the germline genes (accession can be made through GenBank with numbers AY307932 and AY307933). Among eight clones analyzed in total, AM2.9 was isolated seven times and AM3.26 only one time, respectively.
[b]Differences in nucleotides from $V_H$ and $V_K$ germline sequences.
[c]Differences in amino acid sequences of $V_H$ and $V_L$ CDR3 regions of selected scFv from germline-determined regions.

Discussion

We have selected a number of anti-Aβ42 scFv antibodies using an immune anti-Aβ42 scFv antibody library. The analysis of nucleotide sequences of eight isolated scFv clones resulted in identification of only two unique clones with extensive hypermutations, particularly in CDR regions, indicating that antigen-driven immune response was occurring in Aβ immunized mice. We believe that there is no need to generate very large immune scFv antibody libraries to isolate antigen-specific scFv clones, since generally, hyperimmunization induces oligoclonal immune responses, as is what probably took place. However, it remains to be seen whether other unique clones are present in the library by modifying biopanning and/or bacterial cell growing conditions and selecting more clones.

In this regard, it is well known that many scFvs are toxic to E. coli cells, therefore, special expression vectors containing inducible promoter regions were designed to express scFvs creating optimal cell growing conditions (Tessmann et al., 2002). Hence, the isolation of our two clones containing UGA (opal) and UAA (ochre) stop codons is the result of scFv-pIII M13 fusion protein expression at low level in bacterial cells allowing their survival. The expression of DNA sequences with these stop codons is not a rare event and, along with the frameshift and ribosome slippage is the part of general mechanism of the regulation of protein expression in E. coli (Carcamo et al., 1998). It was shown that tryptophan (W) is inserted at the UGA stop codon (Mac-Beath and Kast, 1998) and that UGA- and UAA-containing DNA inserts are efficiently expressed in E. coli, which were cloned in phagemid vector pCANTAB 5E, also used in our study (Carcamo et al., 1998). Other evidence that our clones are expressing scFv-pIII fusion protein on M13 phage surface is the application of hyperphage as helper phage, which lacks the M13 gill in phage genome. So, most probably, tryptophan (W) is expressed in our scFv phage clones at the positions of these stop codons in VH FR1 and FR3 regions.

For treatment of AD, anti-Aβ scFv antibodies are of interest and may act both extracellularly and intracellularly (intrabodies). These scFvs can prevent the formation of Aβ aggregates, can dissolve the existing fibrils, pro-fibrils or oligomers as well as, in the case of intrabodies, may bind to intraneuronal deposits of Aβ42. Recent studies demonstrated early intraneuronal accumulation and immunoreactivity of Aβ42 and the presence of stable dimers of Aβ42 in neural cells in culture, before their release into the medium (Selkoe, 2001; Gouras et al., 2000). These observations emphasize the potential therapeutic effect of internalizing antibodies for prevention of intraneuronal Aβ42 aggregation for the treatment of AD.

The therapeutic potential of intrabodies was demonstrated previously for tumor-specific antibodies (Poul et al., 2000) as well as in studies on Huntington disease (Lecerf et al., 2001). As for any passive immunization protocol, one of the advantages of scFv antibodies is the absence of unwanted and deleterious cellular immune response caused by Aβ42 immunization. In addition, since the clearance of Aβ42-scFv complex in vivo would not activate microglia as in the case of full-length antibody, this additional source of inflammation in patients (Lue and Walker, 2002) would be avoided.

It has been demonstrated previously that intranasal administration of a Aβ42-specific scFv antibody displayed on phage targeted Aβ deposition in the brain of live transgenic mice (Frenkel and Solomon, 2002). No visible toxic effects after phage administration were detected in the brain by histology studies. In previous studies (Frenkel et al., 2000; Frenkel and Solomon, 2002), scFv antibodies with a single specificity of a parental IgM that recognized N-terminal linear EFRH region of Aβ42 were evaluated. However, there are reports on the existence of a conformational epitopes on Aβ42 as well as other regions on this molecule involved in fibril formation (Gaskin et al., 1993; Pike et al., 1995; Ma and Nussinov, 2002), and antibodies directed to these regions could be of interest for AD treatment and prevention. Thus, it has been shown that passive administration of monoclonal antibodies directed to the central region of Aβ reverses memory deficits in mice (Dodart et al., 2002) and administration of antibodies directed to C termini of Aβ significantly reduced the number of seizure-induced degenerating cells in the hippocampus (Mohajeri et al., 2002). Also, the higher toxicity of N-truncated amyloid peptides Aβ (12-42) compared with the full-length peptide was demonstrated (Demeester et al., 2001). Moreover, combining of biochemical, spectroscopic and morphologic methods in the recent study by Bitan et al. (Bitan et al., 2003) allowed the further elucidation of the role of Aβ42 Ile-41 residue in promoting the initial oligomerization of Aβ42 and that of Ala-42 residue in facilitating the peptide's self-association.

The major advantage of the approach disclosed in the present Example is the possibility of selection of scFv antibodies directed to different regions of Aβ since our anti-Ah scFv library contains a large pool of antibodies with all possible specificities induced by Aβ immunization in contrast to a library based on the immunoglobulin gene of a single IgM antibody directed to the aminoterminal region of Aβ (Frenkel et al., 2000). Moreover, it has been demonstrated that these anti-amino-terminal antibodies resulted in an increase in cerebral amyloid angiopathy (CAA)-associated microhemorrhages in APP23 transgenic mice (Pfeifer et al., 2002). Identification of antibodies recognizing other linear or conformational epitopes on Aβ42 may help to prevent possible side effects. Our ongoing studies on epitope mapping will give the answer about the nature of epitope recognized by isolated scFv. In conclusion, considering all existing data pointing to a possibility that anti-Aβ antibodies could interfere with AD, the phage-displayed anti-Aβ42 scFv antibodies selected in this study may be of interest for therapeutic use for passive immunization of AD patients after modification with substances that increase their blood-brain barrier permeability.

Example 2

Isolation of Anti-Aβ Antibodies from a Human Phage-Displayed scFv Antibody Library and Production of a Therapeutic Anti-Aβ Peptide from Antibody Sequence A library of phage-displayed human single-chain Fv (scFv) antibodies was selected against the human amyloid-beta peptide (Aβ42). Two new anti-Aβ42 phage displayed scFvs antibodies were obtained and the sequences of their $V_H$ and Vκ genes were analyzed. A synthetic peptide based on the sequence of Ig heavy chain ($V_H$) complementarity-determining region (HCDR3) of the clone with the highest recognition signal was generated and determined to bind to Aβ42 in ELISA. Surprisingly, we showed for the first time that an HCDR3-based peptide had neuroprotective potential against Aβ42 neurotoxicity in rat cultured hippocampal neurons. Our results show that not only scFvs recognizing Aβ42 but also synthetic peptides based on the $V_H$ CDR3 sequences of these antibodies are novel candidates for small molecule-based Alzheimer's Disease therapy. As discussed below, in certain embodiments, such therapeutic peptides may be administered to subjects in the form of a vector, such as an M13 vector, that displays the therapeutic peptides on a surface protein.

Materials and Methods

Selection of A/β-Specific scFV Antibodies by Biopanning Against Aβ42.

A non-immune human scFv antibody library cloned in pHEN1 and containing $6.7 \times 10^9$ members was used, prepared as disclosed in Sheets et al. (1998). Phage particles were rescued from the library using M13KO7 helper phage (Invitrogen, Carlsbad, Calif., USA). Selection and amplification procedures for the scFv library were carried out essentially as described previously (Gevorkian et al., 1998; Manoutcharian et al., 1999; Gevorkian et al., 2000; Manoutcharian et al., 2003) using 96-well MaxiSorp microtiter plates (Nunc, Roskilde, Denmark) coated overnight with 2 µg/ml of wild-type Aβ42 (BACHEM Bioscience Inc., King of Prussia, Pa., USA) in PBS. Wild-type Aβ42 lacked any deletion or substitution mutations in amino acid sequence.

Plates were blocked with PBS containing 2% BSA (PBS/2% BSA), and then the phage were added at a concentration of $10^{12}$/ml. After incubation for 4 hrs at 4° C., the plates were washed with cold PBS containing 0.05% Tween-20 (PBS/Tween), and bound phage was eluted using 100 µl/well of 100 mM Triethylamine. A 1M Tris HCl solution was then added in order to neutralize the eluate. In each round we rescued the enriched phagemid library using helper phage M13K07. Four rounds of biopanning were performed. After the fourth round of biopanning, the eluate was plated and 16 individual clones were picked, rescued using helper phage and analyzed for specific Aβ42 binding by ELISA.

Microtiter plates were coated with Aβ42 and blocked as described above, $10^{10}$ of each phage clone were added, and after incubation for 1 h at 37° C., plates were washed with PBS/Tween. An anti-M13 monoclonal HRP (horseradish peroxidase) conjugate (Amersham Pharmacia Biotech, USA) diluted in PBS/1% BSA was then added to the plates followed by an incubation for 1 h 37° C. Plates were washed and the ABTS (2,2'-azino-bis(3-ethylbenzothiazoline-6-sulfonic acid) single solution (Zymed, San Francisco, Calif., USA) was added. The OD 405 nm readings were measured using Opsys MR Microplate Reader (DYNEX Technologies, Inc., Chantilly, Va., USA). An identical ELISA procedure was performed using Flemish (containing an A to G substitution at aa21; i.e. A21G) and Dutch (containing an E to Q substitution at aa22; E22Q) mutant Aβ42 (SynPep Corp., CA, USA).

DNA Sequencing

DNA sequencing of the $V_H$ and Vκ genes of ELISA positive clones was performed on a Genetic Analyzer ABI PRISM 3100 (Applied Biosystems, Foster City, Calif., USA) using miniprep-purified (Qiagen Inc., Santa Clarita, Calif., USA) double-stranded DNA from the clones and a pair of pHEN1 vector-based primers (Invitrogen). The DNA and deduced amino acid sequences were analyzed with the help of the ExPASy Molecular Biology tools and IMGT (the International ImMunoGeneTics) Information System database. The DNA and amino acid sequences of isolated scFvs were submitted to the GenBank database.

ELISA Using CDR-Based Synthetic Peptides.

The peptides based on the CDR3 sequence of $V_H$ from clone 4.4 with and without amino- and carboxy-terminal cysteines were purchased from Invitrogen. These peptides were: N44 (ASVRGWYVRSVFDPA SEQ ID NO:1) and C44 (CASVRGWYVRSVFDPAC SEQ ID NO:2). Two alanine and two cysteine residues were added to the HCDR3 sequence. The non-related cyclic peptide GM15 (IWGCS-GKLICTTAVP SEQ ID NO:3) as well as the scrambled cyclic peptide ScrC44 (CADWRYRSVFGPVSVAC SEQ ID NO:4) were synthesized at our facilities by standard Fmoc strategy. Peptides were purified on reverse phase high performance liquid chromatography column (Delta Pack, Waters Co., Milford, Mass., USA) with a linear gradient of 5-80% acetonitrile in 0.1% aqueous trifluoroacetic acid over 30 min at 0.7 ml/min.

ELISA analysis was carried out using MaxiSorp microtiter plates coated overnight with synthetic peptide at a concentration of 10 µg/ml in carbonate buffer. After washing, plates were blocked with PBS/2% BSA for 1 h at 37° C. After incubation and a washing step, biotinylated Aβ42 was added to each well. Plates were again incubated for 1 h at 37° C., washed, and reacted with an avidin-peroxidase conjugate diluted 1:500 (Pharmingen, San Jose, Calif., USA) followed by the ABTS single solution (Zymed) as described above.

For competition ELISA, cyclic C44 and linear N44 were diluted in PBS/1% BSA and incubated with biotinylated Aβ42 overnight at 4° C. prior to addition to plates coated with cyclic C44.

Neuroprotection Assay

Primary cultures of hippocampal neurons were prepared from 17-18 day gestational Wistar rat embryos as described previously (Brewer et al., 1993) with some modifications (Massieu et al., 2003). Briefly, after dissection, 10-12 hippocampi were chopped into 300-µm cubes, incubated in a 0.25% trypsin solution, and dispersed by trituration in a 0.08% DNAase and 0.52% soybean trypsin inhibitor containing solution. Cells were suspended in Neurobasal culture medium (GIBCO/Life technologies, Rockville Md., USA) (Brewer et al. 1993) supplemented with B27 (Minus AO GIBCO/life technologies, Rockville, Md., USA), 0.5 mM L-glutamine, 20 µg/ml gentamicin, and 0.2 mM glutamate, and plated at a density of $260-290 \times 10^3/cm^2$ in Costar 48-well plates (Cambridge, Mass., USA), precoated with poly-L-lysine (5 µg/ml). Cells were cultured for 6 days in vitro (DIV) at 37° C. in a humidified 5% $CO_2$/95% air atmosphere. Glucose (5 mM) and cytosine arabinoside (10 µM) were added to cultures 4 days after plating. The neuronal population in this culture was 95% of the total cells as determined by immunocytochemistry against microtubule-associated protein (MAP-2) and glial fibrillary acidic protein (GFAP), neuronal and glial cell markers, respectively (not shown).

Cultures were exposed to wild-type Aβ42 (40 µM) during 72 h either in the presence or absence of the different synthetic peptides (N44 and C44, 40 µM). The effect of individual treatments of the different peptides on cell viability was also tested. Aβ42 was pre-incubated at 37° C. during 48 h to promote its aggregation and increase neurotoxicity. Cell viability was assessed by the MTT (3-(4,5-dimethylthiazol-2-yl)-2,5-diphenyltetrazolium bromide) dye reduction assay (Mosmann, 1983) as previously described (Garcia and Massieu, 2001). The assay is based on the ability of living mitochondria to convert MTT into insoluble formazan by active dehydrogenases.

In brief, 72 h after exposure to Aβ42, cell cultures were incubated with MTT (150 µM) during a 1 h period at 37° C. in a 5% $CO_2$/95% $O_2$-containing atmosphere. The medium was aspirated, and the precipitated formazan was solubilized with 0.480 ml isopropanol. After solubilization, isopropanol was transferred to eppendorf tubes, centrifuged (18 000 rpm for 30 s) and the optical density in the supernatant measured at 570 nm in a spectrofluorometer (Beckman DU-640). Cell damage was expressed as percent reduction in mitochondrial activity relative to control cultures. Data were expressed as means±SE (standard error) of 4 independent experiments. All experiments with animals were conducted using protocols approved by our Institutional Animal Care Committee.

Statistical Analysis.

In order to evaluate the significance of the difference between scFv displaying phage and wild type phage as well as HCDR3-based peptide and the non-related peptide, the t-test statistical analysis for paired samples was performed. For multiple comparisons ANOVA and post-hoc LSD test were used. SAS (SAS Institute Inc., Cary, N.C. 27511, USA, 6.02) statistical software program was employed.

Results

Selection of Aβ-Specific scFv Antibodies by Biopanning Against Aβ and ELISA Screening of selected scFvs.

Figure 2:
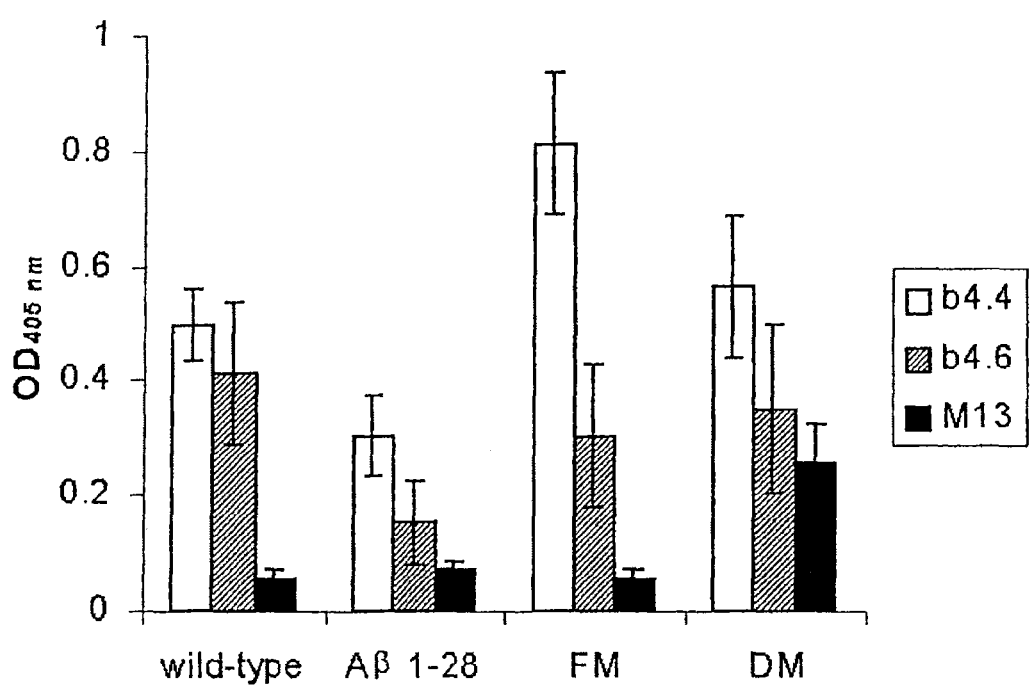
FIG. 2. ELISA analysis of binding of two phage-displayed scFv antibodies to Aβ42 (wild-type as well as to mutant Aβ42 containing the Flemish or Dutch mutations) and Aβ1-28. Phage expressing human scFv antibodies (b4.4 and b4.6) were added to plates coated with the different human Aβ-peptides or a non-related control peptide. Wild type phage (M13) was used as a negative control. Mouse anti-Aβ42 serum was used as a positive control and showed $OD_{405}$=2.29±0.022. Data are means±SE of 3 independent experiments. Differences between binding of b4.4 and M13 to all four Aβ peptides were statistically significant ($p<0.05$). Differences between binding of b4.6 and M13 to wild-type and Flemish mutation Aβ42 were statistically significant ($p<0.05$), but no statistically significant differences for binding to Aβ1-28 and Dutch mutation Aβ42 were observed.

The non-immune human scFv library displayed on phage was selected against the human Aβ42 peptide. After the first round of selection, the titer of recovered phage was 1×10³. Recovery of the phage increased to 2×10⁶, 6×10⁶ and 1×10⁷ after the second, third and fourth rounds of panning, respectively. After the fourth round of bioselection, 16 individual clones were randomly picked and evaluated in ELISA using the Aβ42 peptide. OD readings of the two clones with the highest signal (i.e. b4.4 and b4.6) are shown in FIG. 2. These two clones were also tested for binding to Flemish and Dutch mutants, as well as to Aβ1-28 (FIG. 2). Wild type phage was used as a negative control to measure non-specific interactions between phage and Aβ. Also, each phage-displayed scFv was tested for binding to control non-related peptide to exclude non-specific binding. While phage b4.4 recognized all three Aβ42 peptides as well as Aβ1-28, phage b4.6 bound only to wild type Aβ42 and Flemish mutant (FIG. 2). Binding of phage b4.6 to Aβ42 containing the Dutch mutation and Aβ1-28 was not statistically different from control phage M13.

Sequence Analysis.

The nucleotide sequences of the V$_H$ and V$_L$ genes of the two selected clones were determined and aligned to the most homologous germline genes/segments in the IMGT and VBASE directories (Table 2). DNA sequence analysis of these clones revealed that they have only a few nucleotide and amino acid changes through comparison of the closest germline sequences including those at the V$_H$ (D) J$_H$ and V$_K$J$_K$ junction regions. The V$_H$ gene of the clone b4.4 derives from DP47 V$_H$ gene, the most frequently expressed human V$_H$ gene (Tomlinson et al., 1992), which was also over-represented in the V-gene repertoire of the scFv library used in our study (Sheets et al., 1998). The heavy chain CDR3 of the clone b4.4 contains 15 amino acids (SVRGWYVRSVFDP, SEQ ID NO:10), while the same region of the clone b4.6 contains only 8 amino acids (SHYWDS, SEQ ID NO:11). No sequence homology was found between these two HCDR3 regions. The nucleotide and amino acid sequences of the scFv clones isolated are available at GenBank Accession Nos. AY454122 and AY454123. The amino acid sequences are as disclosed below.

```
clone 4.4
                                           (SEQ ID NO: 13)
QAQLVESGGGLVQPGGSLRLSCAASGFTFSSYAMSWVRQAPGKGLE
WVSAISGSGGSTYYADSVKGRFTISRDNSKNTLYLQMNSLRAEDTA
VYYCAKSVRGWYVRSVFDPWSQGTLVTVSSGGGGSGGGGSGGGGSE
IVLTQSPSSLSASVGDRVTITCRASQGISHHLAWFQQKAGKAPKLL
IYGTSSLQSGVPSRFSGSGSGTDFTLTNSSLQSEDFATYYCLQDYN
FPYTFGQGTKLEIKR
```

It will be apparent to the skilled artisan that peptides based on all or part of the human HCDR3 sequences and/or all or part of the human scFv sequences may be of use to treat subjects with AD or subjects at risk of developing AD.

ELISA Using CDR3-Based Synthetic Peptides.

Synthetic peptide based on the HCDR3 sequence of the clone b4.4 was prepared. The peptide was designed to be 17 amino acids in length including two alanines added at each end (peptide N44). Also, another peptide with the same 17 amino acids, but containing an additional cysteine at each end to mimic the loop structure of the CDR (peptide C44), as well as a scrambled peptide with the cysteines at ends (peptide Scr44) were prepared.

Figure 3:
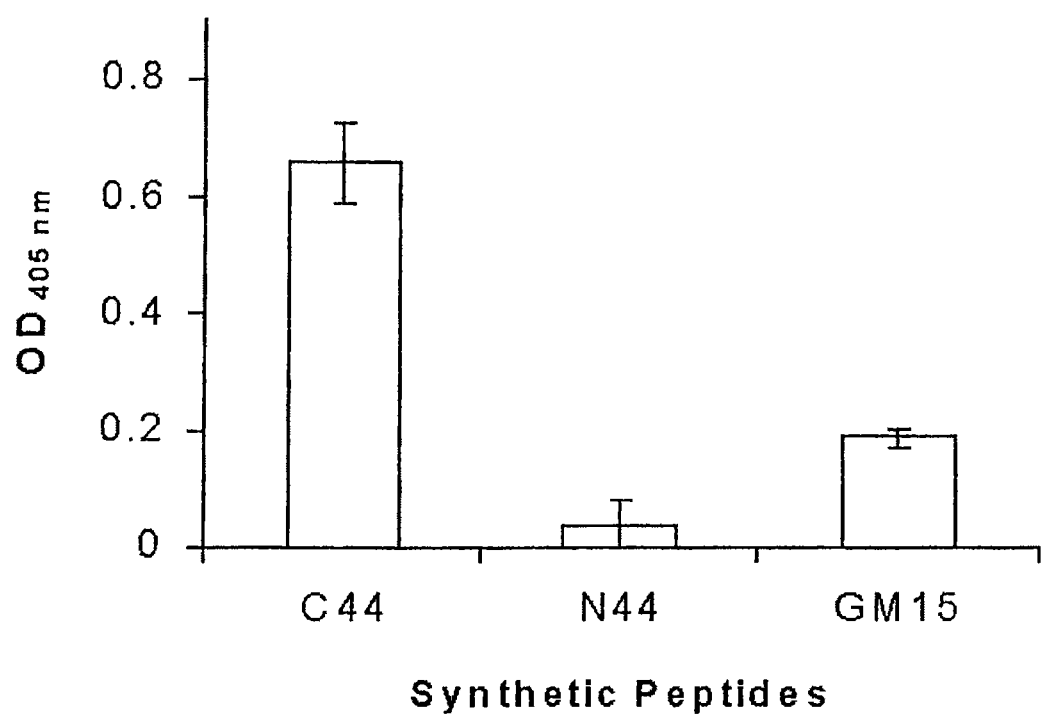
FIG. 3. Binding of HCDR3-derived synthetic peptides to Aβ42 in ELISA. Biotinylated Aβ42 was added to plates coated with HCDR3-derived synthetic peptides N44 (a peptide without cysteine) and C44 (a peptide containing two cysteines, in cyclic form). GM15 is a non-related cyclic peptide that was used as a negative control. Also, Scr44 peptide in cyclic form was used as a negative control and demonstrated an $OD_{405}$=0.25±0.03. Data are means±SE of 3 independent experiments. Differences between binding of Aβ42 to cyclic C44 and linear N44 or control non-related cyclic GM15 were statistically significant ($p<0.05$).
Figure 4:
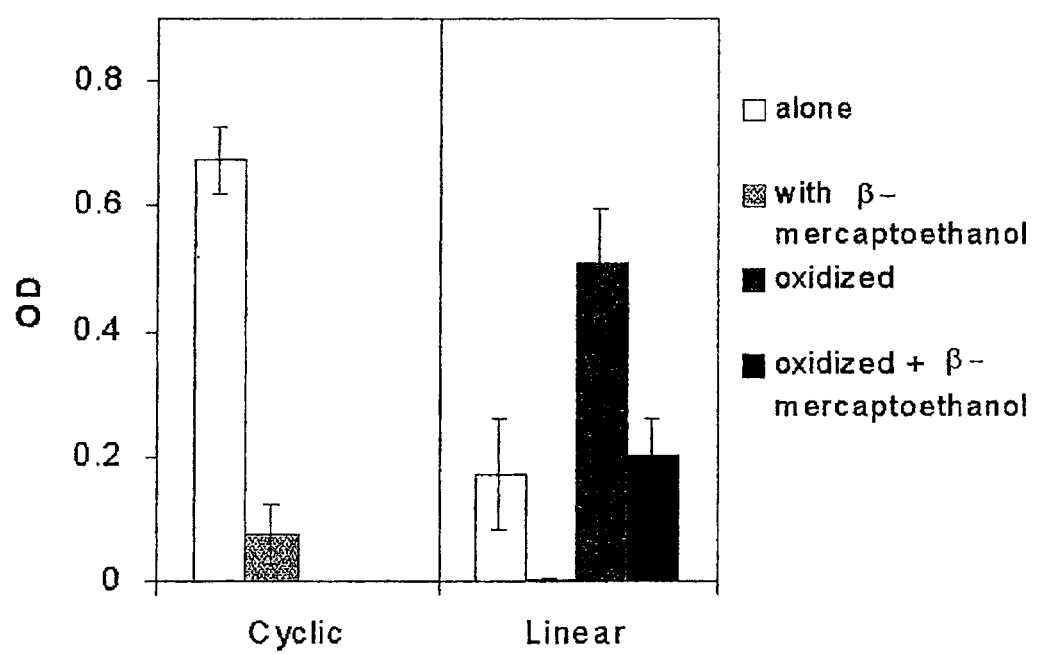
FIG. 4. Binding of HCDR3-derived peptide containing two cysteines in either reduced or oxidized form to Aβ42. The cyclic peptide was treated with β-mercaptoethanol and the linear peptide was first air oxidated and subsequently this oxidated aliquot was treated with β-mercaptoethanol. Data are means±SE of 3 independent experiments. Difference between binding of Aβ42 to C44 in cyclic and linear forms (i.e. in the presence of beta-mercaptoethanol) was statistically significant ($p<0.05$). Also, difference between binding of Aβ42 to oxidized and subsequently reduced linear C44 was statistically significant ($p<0.05$).
Figure 5:
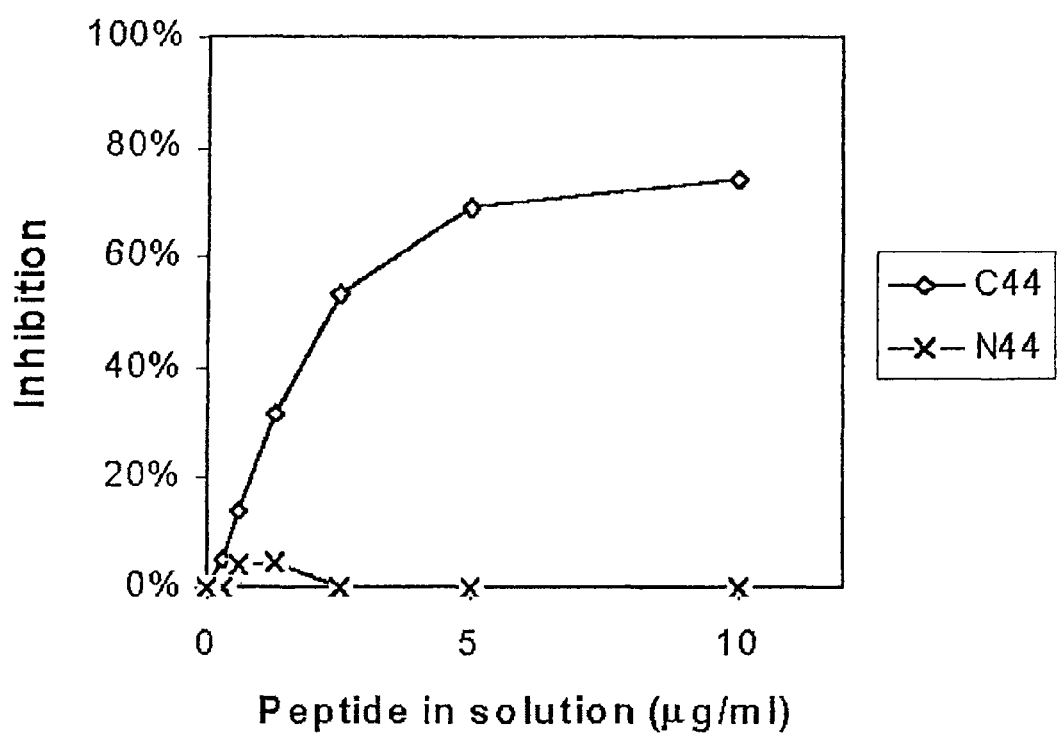
FIG. 5. Competition assay measuring the inhibition of binding of biotinylated Aβ42 to cyclic C44 in the presence of cyclic C44 or linear N44. Competition was not observed when the linear N44 was added to the PBS/1% BSA/Aβ42 solution. Addition of cyclic C44 to Aβ42 in solution inhibited, in a dose dependent manner, the binding of Aβ42 to immobilized cyclic C44.

Although peptide C44 has two cysteines, it may exist either in linear or cyclic form depending on the buffer used. We routinely performed HPLC analysis simultaneously with binding to Aβ42 in ELISA to ensure which form (i.e. linear or cyclic) existed at the time of assay. Peptide N44 did not demonstrate binding to Aβ42 (FIG. 3), while peptide C44 in cyclic form recognized Aβ42. However, a control non-related cyclic peptide GM15 (IWGCSGKLICTTAVP SEQ ID NO:3) (FIG. 3), as well as the cyclic peptide with scrambled amino acids Scr44 (CADWRYRSVFGPVSVAC SEQ ID NO:4) did not bind to Aβ42 (not shown). Peptide C44 in its linear form showed only a weak recognition due to the presence of a low percent of the cyclic form in this sample (FIG. 4). Also, we used β-mercaptoethanol to reduce the S—S bond in the cyclic peptide, and showed that this reduction abolished completely the binding to Aβ42 (FIG. 4). Spontaneous air oxidation of the linear form under strong overnight agitation restored the binding to Aβ42 (FIG. 4). In addition, peptide C44 in cyclic form inhibited the binding of Aβ42 to cyclic C44 immobilized on plate (FIG. 5). Linear peptide N44 did not show any inhibition in the competition ELISA.

HCDR3-Based Peptide Protects Against Aβ42-Induced Neurotoxicity

TABLE 2

Germline genes/segments and complementarity determining region 3 (CDR3) sequences of scFv antibodies isolated from non-immune human library selected on Aβ42[a].

| Clone | V$_H$ germline | D$_H$ germline | J$_H$ germline | HCDR3 | Vκ germline | J$_L$ germline | LCDR3 |
|---|---|---|---|---|---|---|---|
| 4.4 | IGHV3-23*01 | IGHD6-19*01 | IGHJ5*02 | SVRGWYVRSVFDP | IGKV1-16*01 | IGKJ2*01 | CLQDYNFPYT |
| 4.6 | IGHV4-61*01 | IGHD3-3*01 | IGHJ4*02 | SHYWDS | IGKV1-6*01 | IGKJ4*01 | CLQDSDYPLT |

[a]Human germline V$_H$, Vκ, D$_H$, J$_H$, and J$_L$ segments have been assigned as detailed in the International ImMunoGeneTics Information System (IMGT). The DNA sequences of the clones were aligned for V genes and D and J segments using IMGT/V-QUEST program and were very similar to corresponding germline sequences at both DNA and aminoacid levels (accession may be made through GenBank with numbers AY454122 and AY454123).
The clones 4.4 and 4.6 have GFTFSSYA, ISGSGGST and GGSVSSGNYY, IYSSGST sequences in H chain CDR1 and CDR2, respectively, and QGISHH, GTS and RDIRND, AAS sequences in L chain CDR1 and CDR2, respectively.

```
clone 4.6
                                           (SEQ ID NO: 12)
QVQLQESGPGLVKPSETLSLTCSVSGGSVSSGNYYWTWIRQPPGKG
LEWIGYIYSSGSTSYNPSLMSRVTISLDMSKNQFSLRLTSVTAADT
AVYYCARSHYWDSWSPGTLVTVSSGGGGSGGGGSGGGGSDIVMTQS
PSSMSASVGDTVTIACRASRDIRNDLAWYQQKPGKAPKLLIYAASR
LQSGVPSRFSGSGSFTDFTLTIQLCLQPDDFATYYCLQDSDYPLTF
GGGTKLEIKR
```

Figure 6:
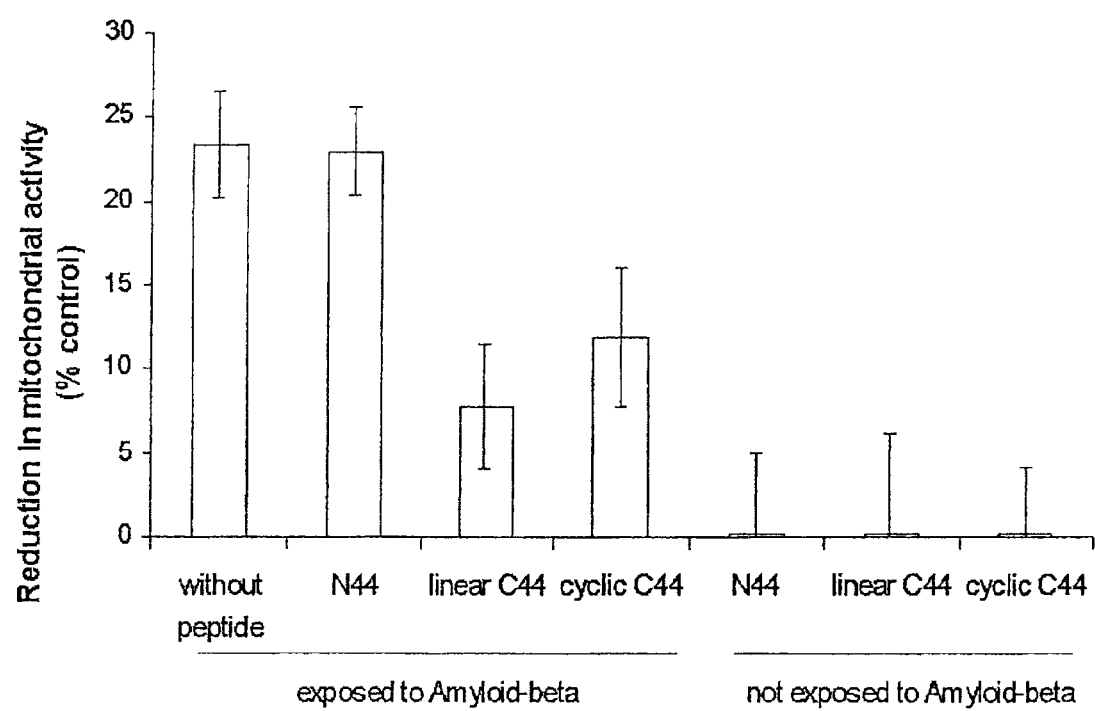
FIG. 6. Effect of HCDR3-derived synthetic peptides on Aβ42-induced neurotoxicity. At 6 DIV hippocampal cultures were exposed to Aβ42 peptide in the presence or absence of the synthetic peptides N44 and C44. N44 and C44 were also incubated with hippocampal cultures alone for 48 h. At the end of the experiment cell viability was assessed by the MTT reduction assay. Data presented are means±SE of 4 independent experiments. Differences between the C44 in cyclic or linear form and Aβ42 alone or N44 were statistically significant ($p<0.05$). Difference between cyclic and linear C44 was not statistically significant.

Similarly to previous studies (Pike et al., 1997; Ueda et al., 1997; Bastianetto et al., 2000), exposure of cultured hippocampal neurons to Aβ42 induced a significant decrease (24.3%) in mitochondrial activity after 72 h (FIG. 6). The presence of the synthetic peptide N44 did not prevent the reduction in mitochondrial activity induced by Aβ42. In contrast, C44 peptide, in its linear form, significantly prevented Aβ42 neurotoxicity. When co-incubated with Aβ42, mitochondrial activity was reduced only 7.7% (FIG. 6). This demonstrated, then, a 69.3% neuroprotective effect. C44 peptide in its cyclic form also showed protection, leading to 11.9% decrease in mitochondrial activity when co-incubated with Aβ42 (a 53.6% neuroprotective effect). Neither N44 nor C44 (either the linear or cyclic forms) alone altered basal MTT reducing capacity (FIG. 6).

Discussion

We have selected two anti-Aβ42 scFv antibodies using a non-immune human phage-displayed scFv antibody library and analyzed the sequences of their $V_H$ and $V_K$ genes. Also, we studied the binding of the selected clones to Aβ1-28 as well as to Flemish and Dutch mutants of Aβ42. Clone b4.4 proved to bind to Aβ1-28 indicating that this scFv antibody recognized an epitope within the first 28 amino acids of Aβ42. Phage b4.6 did not bind to Aβ1-28 suggesting that it recognized another epitope of Aβ42. The Flemish mutant Aβ42 was shown to bind to both phage clones, but the Dutch mutant Aβ42 recognized only phage b4.4. These results suggest that it may be important to search for antibodies specific for wild-type as well as mutant Aβ42 peptides to provide an array of potentially immunotherapeutic reagents against AD. Finally, we performed further characterization of the most positive clone b4.4 by evaluating the HCDR3-based synthetic peptide by ELISA binding to Aβ42 as well as in an in vitro neuroprotection assay.

All previous studies on passive immunotherapy against AD used murine polyclonal and monoclonal antibodies or their fragments (Fab and scFv) which may have limited application in humans due to the possibility of a human anti-mouse immune response. Even if the immunoreactivity to the mouse antibody could be reduced, for example by "humanization" of the mouse sequence, the uptake of large antibody fragments across the blood-brain barrier may be limited. Identification of human antibodies or their fragments may be useful for overcoming this limitation. For AD, anti-β scFv antibodies are of great interest, since, after peripheral administration they can reduce brain Aβ burden via different mechanisms as previously described (Bard et al., 2000; Bacskai et al., 2002; DeMattos et al., 2001; Das et al., 2003; Lernere et al., 2003). Also, they can prevent the formation of Aβ aggregates. In addition, they may enter into neuronal cells and bind to intra-neuronal deposits of Aβ.

Recent studies have demonstrated early intraneuronal accumulation and immunoreactivity of Aβ42 as well as the presence of stable dimers of Aβ42 in neural cells in culture before their release into the medium (Gouras et al., 2000; Gyure et al., 2001; Selkoe, 2001). These observations emphasize the potential therapeutic effect of internalizing anti-Aβ42 scFv antibodies for the treatment of AD. Human scFv intrabodies were previously used to counteract the in situ Huntington aggregation in cellular models of Huntington disease (Lecerf et al., 2001).

Another advantage of the present invention, besides the use of human versus murine antibodies, is the possibility of selecting a panel of antibodies with a range of different specificities. In previous studies by Frenkel et al. (Frenkel et al., 2000; Frenkel and Solomon, 2002), scFv antibodies with the single specificity of their parental murine IgM that recognized N-terminal linear EFRH region of Aβ42 were evaluated. However, side effects such as microhemorrhages, were observed after passive administration of a mouse monoclonal anti-amino terminal Aβ antibody in APP23 transgenic mice (Pfeifer et al., 2002). Also, it has been shown that amino-terminal truncated Aβ species are early, pathological and abundant antigens occurring during the pathogenesis of AD, indicating their potential usefulness as targets for vaccination strategies that could prevent an undesirable immune reaction (Sergeant et al., 2003).

There are reports on the existence of conformational epitopes in Aβ42 as well as other regions on this molecule involved in fibril formation (Gaskin et al., 1993; Pike et al., 1995; Ma and Nussinov, 2002), and antibodies directed to these regions have been shown to reverse memory deficits in mice (Dodart et al., 2002) and to reduce the number of seizure-induced degenerating cells in the hippocampus (Mohajeri et al., 2002). Finally, in a recent study by Miller et al. it was shown that rabbit anti-fibrillar Aβ antibodies recognizing the amino terminus of Aβ1-42 possessed enhanced affinity for vascular amyloid deposits, and this might explain the development of severe meningeal inflammation in patients that had previously been reported (Miller et al., 2003). Moreover, since the amino terminal sequence of Aβ42 (residues 4-10) is shared with the cell associated and circulating 13-APP, and the cell associated β-secretase-generated 13-APP carboxy-terminal fragment, the consequences of treating humans with anti-amino terminal antibodies could potentially have additional undesirable autoimmune effects (Miller et al., 2003). Through the use of phage displayed scFv antibody libraries it is possible to select antibodies to various linear and/or conformational epitopes within Aβ42.

Passive administration of scFv antibodies is not expected to induce the deleterious cellular immune response. In addition, since the clearance of the Aβ42-scFv complex in vivo would not activate microglia as in the case of the full-length antibody due to the lack of the Ig Fc portion, this additional source of inflammation in patients (Lue and Walker, 2002) would be also avoided. It is proposed that scFvs may be administered when displayed on the M13 phage surface. It has been previously demonstrated that intranasal administration of an Aβ42-specific scFv antibody displayed on phage targeted Aβ deposition in the brain of live transgenic mice (Frenkel and Solomon, 2002). No visible toxic effects after phage administration were detected in the brains by histological studies. Soluble scFv are also readily available and may be used in transgenic mice as an alternative to the phage-displayed scFvs.

In a scFv, framework regions separate the CDRs, which are the hypervariable regions of the Ig molecule that interacts with the antigen. Ig heavy chain CDR3 is known to be generally the most variable and to have a predominant participation in antigen-antibody interactions. There are previous reports on biologically active CDR-based peptides which possessed the specificity of the parent antibody (Levi et al., 1993; Bourgeois et al., 1998; Dong et al., 2003; Zinger et al., 2003).

The utilization of CDR-based peptide may overcome several disadvantages of the full-length antibody as well as Fab or scFv fragments. The antiglobulin response is considered a major problem in the clinical development of therapeutic antibodies. To generate functional antibodies with reduced immunogenic side effects, successive technical developments were implied, and domain antibodies (dAbs) that are either the variable domain of an antibody heavy chain or the variable region of an antibody light chain (Holt et al., 2003) were reported and suggested to become the next generation of antibody-based therapeutics. However, Ig heavy chain CDR3-derived peptides may be considered as the smallest antigen binding unit of the antibody and may offer additional advantages (chemical synthesis in endless quantities in controlled conditions and a lower probability of induction of harmful immune response among others) along with advantages of other fragments (Fab, scFv or dAbs).

In the present disclosure we describe for the first time an Ig heavy chain CDR3-derived peptide binding to Aβ42. We have demonstrated that the conformation of CDR-based peptides was important since only the cyclic form bound to Aβ42 in ELISA. This is not surprising, since in the Ig molecule the CDRs comprise loops. In addition, the fact that in bioselection procedures Aβ42 was immobilized on a microtiter plate, and in ELISA experiments the Aβ42 was in a non-immobilized form (i.e. diluted in PBS/1% BSA and added to plates coated with HCDR3-based peptide), indicates that this HCDR3 peptide recognizes an epitope present in both conformations of Aβ42.

We demonstrated for the first time that an Ig HCDR3-based peptide prevented the decrease in mitochondrial activity induced by Aβ42. The peptide containing cysteines in both linear and cyclic forms had protective effect while the linear peptide without N- and C-terminal cysteines was not protective. Moreover, the peptide C44 in the linear form showed a trend toward higher protection compared with the same peptide in cyclic form. Since we do not know the exact structure of the peptide with the two cysteines in experimental conditions used (i.e. it may spontaneously cyclicize or form dimers and/or oligomers), oligomerization of the HCDR3-based peptide may have had a positive effect on neuroprotection. Alternatively, the linear form of C44 may have exhibited increased uptake into a cellular or subcellular compartment, with subsequent formation of the cyclic peptide. Linear monomer N44 that have does not any cysteine residue for oligomer formation did not demonstrate protection, indicating that oligomerization or formation of a cyclic form of linear C44 may indeed play a role in neuroprotection. These results show the protective effect of the HCDR3-based peptide for treatment of AD.

It is likely that modification of scFvs with moieties that increase their blood-brain barrier permeability would improve their efficacy for AD, but they could be used without any modification if they are be capable of sequestering plasma Aβ42, thus reducing or preventing brain amyloidosis. CDR-based synthetic peptides would appear to exhibit few, if any, contraindications that would limit their utility. Likewise, the use of D-amino acids would make them more stable against proteolytic degradation in vivo. Synthesis of peptides utilizing D-instead of L-amino acids is well within the ordinary skill in the art and such peptides may be commercially purchased from known sources.

Example 3

Additional Anti-Aβ Antibodies from a Human Phage-Displayed scFv Antibody Library A library of phage-displayed human single-chain Fv (scFv) antibodies was selected against the human amyloid-beta peptide (Aβ42) using the protocols disclosed in Example 2 above. Two new anti-Aβ42 phage displayed scFvs antibodies were obtained and the sequences of their $V_H$ and Vκ genes were analyzed (not shown). The new scFv clones 4.9 and 4.14 had HCDR3 sequences of DRKGGSFDY (SEQ ID NO:8) and QRGDY (SEQ ID NO:9) respectively. As discussed above, those sequences may be used to design synthetic peptides to administer to AD patients or to subjects at risk of developing AD. The skilled artisan will realize that addition of cysteines at both ends of the peptide to facilitate formation of a cyclic peptide may be advantageous for some applications.

Example 4

Administration of Therapeutic Peptides in M14 Phage to Subjects with AD

The administration of scFv anti-Aβ binding peptides displayed as surface proteins on vectors, such as M13, to subjects for therapeutic treatment of AD symptoms is known in the art (see, e.g., U.S. Pat. No. 6,703,015, the text of which from Col. 26, line 47 through Col. 27, line 25 and from Col. 32, line 50 through Col. 33, line 32 is incorporated herein by reference). In an exemplary embodiment, peptides of amino acid sequences corresponding to SEQ ID NO:1, SEQ ID NO:2, SEQ ID NO:7, SEQ ID NO:8, SEQ ID NO:9, SEQ ID NO:10, SEQ ID NO:11, SEQ ID NO:12 and SEQ ID NO:13 are inserted in pHEN1 as detailed in Example 2 above. Phage particles are rescued using M13KO7 helper phage. Amplification of phage is carried out as described previously (Gevorkian et al., 1998; Manoutcharian et al., 1999; Gevorkian et al., 2000; Manoutcharian et al., 2003). Expression of the cloned inserts is confirmed by binding assays to Aβ42 peptide, as disclosed in Examples 1 and 2.

PDAPP transgenic mice are divided into groups and the groups are treated by intranasal administration with $10^{10}$ amplified phage expressing the peptide sequences. A different therapeutic peptide is administered to each group. Mice are decapitated at 1, 14 and 28 days after phage administration and brain tissue is removed, fixed and processed for histopathology as disclosed in U.S. Pat. No. 6,703,015. Biotinylated scFv antibody against Aβ42 peptide is used to stain for the presence of amyloid plaques.

At 14 and 28 days after administration of peptide displaying phage, the brains of PDAPP mice show a decrease in the presence of amyloid plaques. Control mice treated with vector alone or mice treated with a non-specific phage displayed peptide (SEQ ID NO:3) show no change in the level of amyloid plaques.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in their elements or in the sequence of elements of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Arap, W., Pasqualini R., and Ruoslahti, E. Cancer treatment by targeted drug delivery to tumor vasculature. Science 279:377-380, 1998.
Bacskai, B. J., Kajdasz, S. T., McLellan, M. E., Games, D., Seubert, P., Schenk, D., Hyman, B. T, 2002. Non-Fc-mediated mechanisms are involved in clearance of amyloid-β in vivo by immunotherapy. J. Neuroscience 22, 7873-7878.
Barany and Merrifield, The Peptides, Gross and Meienhofer, eds., Academic Press, New York, pp. 1-284, 1979.
Bard, F., Cannon, C., Barbour, R., Burke, R. L., Games, D., Grajeda, H., Guido, T., Hu, K., Huang, J., Johnson-Wood, K., Khan, K., Kholodenko, D., Lee, M., Lieberburg, I., Motter, R., Nguyen, M., Soriano, F., Vasquez, N., Weiss, K., Welch, K., Seubert, P., Schenk, D., Yednock, T., 2000. Peripherally administered antibodies against amyloid-h peptide enter the central nervous system and reduce pathology in a mouse model of Alzheimer's disease. Nat. Med. 6, 916-919.

Bastianetto, S., Zheng, W-H., Quirion, R., 2000. The *Ginkgo biloba* extract (EGb 761) protects and rescues hippocampal cells against nitric-oxide-induced toxicity: involvement of its flavonoid constituents and protein kinase C. J. Neurochem. 74, 2268-2277.

Bitan, G., Kirkitadze, M. D., Lomakin, A., Vollers, S. S., Benedek, G. B., Teplow, D. B., 2003. Amyloid h-protein (Ah) assembly: Ah40 and Aβ42 oligomerize through distinct pathways. Proc. Natl. Acad. Sci. U.S.A. 100, 330-335.

Bourgeois, C., Bour, J. B., Aho, L. S., Pothier, P., 1998. Prophylactic administration of a complementarity-determining region derived from a neutralizing monoclonal antibody is effective against respiratory syncytial virus infection in BALB/c mice. J. Virol. 72, 807-810.

Brewer, G. J., Torricelli, J. R., Evege, E. K., Price, P. J., 1993. Optimized survival of hippocampal neurons in B27-supplemented neurobasal, a new serum-free medium combination. J. Neurosci. Res. 35, 567-576.

Calhoun, M. E., Burgermeister, P., Phinney, A. L., Stalder, M., Tolnay, M., Wiederhold, K. H., Abramowski, D., Sturchler-Pierrat, C., Sommer, B., Staufenbiel, M., Jucker, M., 1999. neuronal overexpression of mutant amyloid precursor protein results in prominent deposition of cerebrovascular amyloid. Proc. Natl. Acad. Sci. USA. 96, 14088-14093.

Carcamo, J., Ravera, M. W., Brissette, R., Dedova, O., Beasley, J. R., Alam-Moghr, A., Wan, C., Blume, A., Mandecki, W., 1998. Unexpected frameshifts from gene to expressed protein in a phage-displayed peptide library. Proc. Natl. Acad. Sci. U.S.A. 95, 11146-11151.

Das, P., Howard, V., Loosbrock, N., Dickson, D., Murphy, M. P., Golde, T. E., 2003. Amyloid-β immunization effectively reduces amyloid deposition in FcR=$^{-/-}$ knock-out mice. J. Neuroscience 23, 8532-8538.

DeMattos, R. B., Bales, K. R., Cummins, D. J., Dodart, J.-C., Paul, S. M., Holtzman, D. M., 2001. Peripheral anti-Aβ antibody alters CNS and plasma Aβ clearance and decreases brain Aβ burden in a mouse model of Alzheimer's disease. Proc. Natl. Acad. Sci. USA 98, 8850-8855.

Demeester, N., Mertens, C., Caster, H., Goethals, M., Vandekerckhove, J., Rosseneu, M., Labeur, C., 2001. Comparison of the aggregation properties, secondary structure and apoptotoc effects of wild-type, Flemish and Dutch N-terminally truncated amyloid h peptides. Eur. J. Neurosci. 13, 2015-2024.

Dodart, J. C., Bales, K. R., Gannon, K. S., Greene, S. J., DeMattos, R. B., Mathis, C., DeLong, C. A., Wu, S., Wu, X., Holtzman, D. M., Paul, S. M., 2002. Immunization reverses memory deficits reducing Ah burden in Alzheimer's disease model. Nat. Neurosci. 5, 452-457.

Dong, L., Chen, S., Schachner, M., 2003. Single chain Fv antibodies against neural cell adhesion molecule L1 trigger L1 functions in cultured neurons. Mol. Cell. Neurosci. 22, 234-247.

Fassbender, K., Simons, M., Bergmann, C., Stroick, M., Lutjohann, D., Keller, P., Runz, H., Kuhl, S., Bertsch, T., von Bergmann, K., Hennerici, M., Beyreuther, K. and Hartmann, T. "Simvastatin strongly reduces levels of Alzheimer's disease β-amyloid peptides Aβ42 and Aβ40 in vitro and in vivo." *Proc Natl Acad Sci USA* 2001, 98:5856-5861.

Feliche, F. G., Houzel, J. C., Garcia-Abreu, J., Louzada, P. R. F., Afonso, R. C., Meirelles, M. N. L., Lent, R., Neto, V. M., and Ferreira, S. T. "Inhibition of Alzheimer's disease β-amyloid aggregation, neurotoxicity, and in vivo deposition by nitrophenols: implications for Alzheimer's therapy. *FASEB J.* 2001, 15: 1297-1299.

Frenkel, D., Balass, M. and Solomon, B. "N-terminal EFRH sequence of Alzheimer's beta-amyloid peptide represents the epitope of its anti-aggregating antibodies" *J Neuroimmunol* 1998, 88:85-90.

Frenkel, D., Katz, O., Solomon, B. "Immunization against Alzheimer's b-amyloid plaques via EFRH phage administration" *Proc Natl Acad Sci USA* 2000a, 97:11455-11459.

Frenkel, D., Solomon, B. and Benhar, I. Modulation of Alzheimer's β-amyloid neurotoxicity by site-directed single-chain antibody" *J Neuroimmunol* 2000b; 106:23-31.

Frenkel, D., Solomon, B., 2002. Filamentous phage as vector-mediated antibody delivery to the brain. Proc. Natl. Acad. Sci. U.S.A. 99, 5675-5679.

Frenkel, D., Solomon, B., Benhar, I., 2000. Modulation of Alzheimer's β-amyloid neurotoxicity by site-directed single-chain antibody. J. Neuroimmunol. 106, 23-31.

Frenkel, D., Solomon, B., Benhar, I., 2000. Modulation of Alzheimer's hamyloid neurotoxicity by site-directed single-chain antibody. J. Neuroimmunol. 106, 23-31.

Furlan, R., Brambilla, E., Sanvito, F., Roccatagliata, L., Olivieri, S., Bergami, A., Pluchino, S., Uccelli, A., Comi, G., Martino, G., 2003. Vaccination with amyloid-beta peptide induces autoimmune encephalomyelitis in C57/BL6 mice. Brain 126, 285-291.

García, O., Massieu L., 2001. Strategies for neuroprotection against L-trans-2,4-pyrrolidine dicarboxylate-induced neuronal damage during energy impairment in vitro. J Neurosci Res. 64, 418-428.

Gargano, N. and Cattaneo, A. "Inhibition of murine leukaemia virus retrotranscription by the intracellular expression of a phage-derived anti-reverse transcriptase antibody fragment" *J Gen Virol* 1997; 78:2591-2599.

Gaskin, F., Finley, J., Fang, Q., Xu, S., Fu, S. M., 1993. Human antibodies reactive with h-amyloid protein in Alzheimer's disease. J. Exp. Med. 177, 1181-1186.

Gevorkian, G., Manoutcharian, K., Almagro, J. C., Govezensky, T., Dominguez, V., 1998. Identification of autoimmune thrombocytopenic purpura-related epitopes using phage-display peptide library. Clin. Immunol. Immunopathol. 86, 305-309.

Gevorkian, G., Manoutcharian, K., Govezensky, T., Cano, A., Dominguez, V., Santamaria, H., Larralde, C., 2000. Identification of mimotopes of platelet autoantigens associated with autoimmune thrombocytopenic purpura. J. Autoimm. 15, 33-40.

Gevorkian, G., Viveros, M., Zamudio, F. and Larralde, C. Solid-phase synthesis of a peptide comprising the 605-611 disulfide loop of gp41, transmembrane glycoprotein of HIV-1. *Org Prep Proc Int* 1995; 27:375-377.

Gouras, G. K., Tsai, J., Naslund, J., Vincent, B., Edgar, M., Checker, F., Greenfield, J. P., Haroutunian, V., Buxbaum, J. D., Xu, H., Grenngard, P., Relkin, N. R., 2000. Intraneuronal Aβ42 accumulation in human brain. Am. J. Pathol. 156, 15-20.

Gyure, K. A., Durham, R., Stewart, W. F., Smialek, J. E., Troncoso, J. C., 2001. Intraneuronal Aβ-amyloid precedes development of amyloid plaques in Down syndrome. Arch. Pathol. Lab. Med. 125, 489-492.

Hock et al., 2003. Antibodies against β-amyloid slow cognitive decline in Alzheimer's disease. Nature 408, 1-20.

Holt, L. J., Herring, C., Jespers, L. S., Woolven, B. P., Tomlinson, I. M., 2003. Domain antibodies: proteins for therapy. Trends in Biotechnol. 21, 484-490.

Janus, C., Pearson, J., McLaurin, J., Mathews, P. M., Jiang, Y., Schmidt, S. D., Azhar Chishti, M., Horne, P., Heslin, D., French, J., Mount, H. T. J., Nixon, R. A., Mercken, M., Bergeron, C., Fraser, P. E., St. George-Hyslop, P., Westaway, D., 2000. Aβ peptide immunization reduces behavioral impairment and plaques in a model of Alzheimer's disease. Nature 408, 979-982.

Klein, W. L., Krafft, G. A. and Finch, C. E. "Targeting small Aβ oligomers: the solution to an Alzheimer's disease conundrum?" *Trends in Neurosciences* 2001, 24:219-224.

Kotilinek, L. A., Bacskai, B., Westerman, M., Kawarabayashi, T., Younkin, L., Hyman, B. T., Younkin, S., Ashe, K. H., 2002. Reversible memory loss in a mouse transgenic model of Alzheimer's disease. J. Neurosci. 22, 6331-6335.

Lecerf, J.-M., Shirley, T. L., Zhu, Q., Kazantsev, A., Amersdorfer, P., Housman, D. E., Mecer, A., Huston, J. S., 2001. Human single-chain Fv intrabodies counteract in situ huntingtin aggregation in cellular models of Huntington's disease. Proc. Natl. Acad. Sci. USA 98, 4764-4769.

Lernere, C. A., Spooner, E. T., LaFrancois, J., Malester, B., Mori, C., Leverone, J. F., Matsuoka, Y., Taylor, J. W., DeMattos, R. B., Holtzman, D. M., Clements, J. D., Selkoe, D. J., Duff, K. E., 2003. Evidence for peripheral clearance of cerebral Aβ protein following chronic, active Aβ immunization in PSAPP mice. Neurobiol. Dis. 14, 10-18.

Levi, M., Sallberg, M., Ruden, U., Herlyn, D., Maruyama, H., Wigzell, H., Marks, J., Wahren, B., 1993. A complementarity-determining region synthetic peptide acts as a miniantibody and neutralizes human immunodeficiency virus type 1 in vitro. Proc. Natl. Acad. Sci. USA 90, 4374-4378.

Lue, L. F., Walker, D. G., 2002a. Modeling Alzheimer's disease immune therapy mechanisms: interactions of human postmortem microglia with antibody-opsonized amyloid-13 peptide. J. Neurosci. Res. 70, 599-610.

Lue, L. F., Walker, D. G., 2002b. Modeling Alzheimer's disease immune therapy mechanisms: interactions of human postmortem microglia with antibody-opsonized amyloid-β peptide. J. Neurosci. Res. 70, 599-610.

Ma, B., Nussinov, R., 2002. Stabilities and conformations of Alzheimer's h-amyloid peptide oligomers (Ah 16-22, Ah 16-35, and Ah 10-35): sequence effects. Proc. Natl. Acad. Sci. U.S.A. 99, 14126-14131.

MacBeath, G., Kast, P., 1998. UGA read-through artifacts—when popular gene expression systems need a pATCH. BioTechniques 24, 789-794.

Manoutcharian K, Sotelo J, Garcia E, Cano A, Gevorkian G. "Characterization of Cerebrospinal Fluid Antibody Specificities in Neurocysticercosis Using Phage Display Peptide Library." *Clin Immunol* 1999; 91:117-121.

Manoutcharian, K., Acero, G., Munguia, M. E., Montero, J. A., Govezensky, T., Cao, C., Ugen, K., Gevorkian, G., 2003. Amyloid-beta peptide specific single Chain Fv antibodies isolated from an immune phage display library. J. Neuroimmunol. 145, 12-17.

Manoutcharian, Hock, C., Konietzko, U., Streffer, J. R., Tracy, J., Signorell, A., Muller-Tillmanns, B., Lemke, U., Henke, K., Moritz, E., Garcia, E., Wollmer, M. A., Umbricht, D., de Quervain, D. J. F., Hofmann, M., Maddalena, A., Papassotiropoulos, A., Nitsch, R. M., 2003. Antibodies against h-amyloid slow cognitive decline in Alzheimer's disease. Neuron 38, 1-20.

Manoutcharian, K., Sotelo, J., Garcia, E., Cano, A., Gevorkian, G., 1999. Characterization of cerebrospinal fluid antibody specificities in neurocysticercosis using phage display peptide library. Clin. Immunol. 91, 117-121.

Manoutcharian, K., Terrazas, L. I., Gevorkian, G., Acero, G., Petrossian, P., Rodríguez, M., and Govezensky, T. "Phage displayed T-cell epitope grafted into immunoglobulin heavy-chain complementarity-determining regions: an effective vaccine design tested in murine cisticercosis". Infection and Immunity 1999; 67:4764-4770.

Massieu, L., Haces, M. L., Montiel, T., Hernandez-Fonseca K., 2003. Acetoacetate protects hippocampal neurons against glutamate-mediated neuronal damage during glycolysis inhibition. Neuroscience 120, 365-378.

Merrifield R B. Solid phase peptide synthesis. I. The synthesis of a tetrapeptide. *J Am Chem Soc* 1963; 85:2149-2154.

Merrifield, *Science*, 232: 341-347, 1986

Miller, D. L., Currie, J. R., Mehta, P. D., Potempska, A., Hwang, Y.-W., Wegiel, J., 2003. Humoral immune response to fibrillar β-amyloid peptide. Biochemistry 42, 11682-11692.

Mohajeri, M. H., Sainin, K., Schultz, J. G., Wollmer, M. A., Hock, C., Nitsch, R. M., 2002. Passive immunization against β-amyloid peptide protects central nervous system (CNS) neurons from increased vulnerability associated with an Alzheimer's disease-causing mutation. J. Biol. Chem. 277, 33012-33017.

Morgan, D., Diamond, D. M., Gottschall, P. E., Ugen, K., Dickey, C., Hardy, J., Duff, K., Jantzen, P., DiCarlo, G., Wilcock, D., Connor, K., Hatcher, J., Hope, C., Gordon, M., Arendash, G. W., 2000. Aβ peptide vaccination prevents memory loss in an animal model of Alzheimer's disease. Nature 408, 982-985.

Mosmann, T., 1983. Rapid colorimetric assay for cellular growth and survival: application to proliferation and citotoxicity. J Immunol Methods. 65, 55-63.

Munch, G., Robinson, R., 2002. Potential neurotoxic inflammatory responses to Ah vaccination in humans. J. Neural Transm. 109, 1081-1087.

Pasqualini, R. Vascular Targeting with Phage Display Peptide Libraries. The Quart. J. Nucl. Med. 43:159-162, 1999.

Pfeifer, M., Boncristiano, S., Bondolfi, L., Stalder, A., Se'ller, T., Staufenbiel, M., Mathews, P. M., Jucker, M., 2002. Cerebral hemorrhage after passive anti-Ah immunotherapy. Science 298, 1379.

Pike, C. J., Overman, M. J., Cotman, C. W., 1995. Amino-terminal deletions enhance aggregation of h-amyloid peptides in vitro. J. Biol. Chem. 270, 23895-23898.

Pike, C. J., Ramezan-Arab, N., Cotman, C., 1997. β-amyloid neurotoxicity in vitro: Evidence of oxidative stress but not protection by antioxidants. J. Neurochem. 69, 1601-1611.

Poul, M.-A., Becerril, B., Nielsen, U. B., Morisson, P., Marks, J. D., 2000. Selection of tumor-specific internalizing human antibodies from phage libraries. J. Mol. Biol. 301, 1149-1161.

Rajotte D and Ruoslahti E. Membrane dipeptidase is the receptor for a lung-anti-Aβ binding peptide identified by in vivo phage display. J Biol Chem 274:11593-11598, 1999

Rondot, S., Koch, J., Breitling, F., Dubel, S., 2001. A helper phage to improve single-chain antibody presentation in phage display. Nat. Biotechnol. 19, 75-78.

Schenk, D., Barbour, R., Dunn, W., Gordon, G., Grajeda, H., Guido, T., Hu, K., Huang, J., Johnson-Wood, K., Khan, K., Kholodenko, D., Lee, M., Liao, Z., Lieberburg, I., Motter, R., Mutter, L., Soriano, F., Shopp, G., Vasquez, N., Vandevert, C., Walker, S., Wogulis, M., Yednock, T., Games, D., Seubert, P., 1999. Immunization with amyloid-h attenuates Alzheimer-disease-like pathology in the PDAPP mouse. Nature 400, 173-177.

Selkoe, D. J., 2001. Alzheimer's disease: genes, proteins, and therapy. Physiological Rev. 81, 741-766.

Sergeant, N., Bombois, S., Ghestem, A., Drobecq, H., Kostanjevecki, V., Missiaen, C., Wattez, A., David, J.-P., Vanmechelen, E., Sergheraert, C., Delacourte, A., 2003. Truncated beta-amyloid peptide species in pre-clinical Alzheimer's disease as new targets for the vaccination approach. J. Neurochem. 85, 1581-1591.

Sheets, M. D., Amersdorfer, P., Finnern, R., Sargent, P., Lindqvist, E., Shier, R., Hemingsen, G., Wong, C., Gerhart, J. C., Marks, J. D., 1998. Efficient construction of a large nonimmune phage antibody library: the production of high affinity human single-chain antibodies to protein antigens. Proc. Natl. Acad. Sci. USA 95, 6157-6162.

Smith, G. P. 1985. Filamentous fusion phage: novel expression vectors that display cloned antigens on the virion surface. Science 228:1315-7.

Smith, G. P. Surface presentation of protein epitopes using bacteriophage expression systems. Curr. Opin. Biotechnol. 2:668-673, 1991.

Smith, D. B., and K. S. Johnson. 1988. Single-step purification of polypeptides expressed in Escherichia coli as fusions with glutathione S-transferase. Gene 67:31-40.

Smith G P, and Scott J K. Searching for peptide ligands with an epitope library. Science 228:1315-1317, 1985

Smith G P, and Scott J K. Libraries of peptides and proteins displayed in filamentous phage. Meth. Enzymol. 21:228-257, 1993.

Solomon, B., Koppel, R., Frankel, D., Hanan-Aharon, E., 1997. Disaggregation of Alzheimer h-amyloid by site-directed mAb. Proc. Natl. Acad. Sci. U.S.A. 94, 4109-4112.

Solomon, B., Koppel, R., Hanan, E., and Katzay., T. "Monoclonal antibodies inhibit in vitro fibrillar aggregation of the Alzheimer β-amyloid peptide" Proc Natl Acad Sci US 1996; 93:452-255.

Stewart and Young, Solid Phase Peptide Synthesis, 2d. ed., Pierce Chemical Co., 1984.

Sturchler-Pierrat, C., Abramowski, D., Duke, M., Wiederhold, K.-H., Mistl, C., Rothacher, B., Burki, K., Frey, P., Paganetti, P. A., Waridel, C., Calhoun, M. E., Jucker, M., Probst, A., Staubenbiel, M., Sommer, B., 1997. Two amyloid precursor protein transgenic mouse models with Alzheimer disease-like pathology. Proc. Natl. Acad. Sci. USA 94, 13287-13292.

Tam et al., J. Am. Chem. Soc., 105:6442, 1983.

Tessmann, K., Erhardt, A., Haussinger, D., Heintges, T., 2002. Cloning and molecular characterization of human high affinity antibody fragments against Hepatitis C virus NS3 helicase. J. Viol. Methods 103, 75-88.

Thorsett, E. D. and Latimer, L. H. "Therapeutic approaches to Alzheimer's disease" Curr Opin Chem Biol 2000, 4:377-382.

Tomlinson, I. M., Walter, G., Marks, J. D., Liewelyn, M. B., Winter, G., 1992. The repertoire of human germlineVH sequences reveals about fifty groups of VH segments with different hypervariable loops. J. Mol. Biol. 227, 776-798.

Ueda K., Shinohara S., Yagami T., Asakura K., Kawasaki K. 1997. Amyloid 13 protein potentiates $Ca^{2+}$ influx through L-type voltage-sensitive $Ca^{2+}$ channels: a possible involvement of free radicals. J. Neurochem. 68, 265-271.

U.S. Pat. No. 3,817,837
U.S. Pat. No. 3,850,752
U.S. Pat. No. 3,939,350
U.S. Pat. No. 3,996,345
U.S. Pat. No. 4,215,051
U.S. Pat. No. 4,277,437
U.S. Pat. No. 4,275,149
U.S. Pat. No. 4,366,241
U.S. Pat. No. 4,472,509
U.S. Pat. No. 4,554,101
U.S. Pat. No. 5,021,236
U.S. Pat. No. 5,223,409
U.S. Pat. No. 5,622,699
U.S. Pat. No. 6,068,829

Zinger, H., Eilat, E., Meshorer, A., Mozes, E., 2003. Peptides based on the complementarity-determining regions of a pathogenic autoantibody mitigate lupus manifestations of $(NZB \times NZW)F_1$ mice via active suppression. Int. Immunol. 15, 205-214.

What is claimed is:

1. A composition comprising one or more peptides that bind to human amyloid-beta, wherein the one or more peptides comprise one or more peptides comprising the amino acid sequence of SEQ ID NO: 13.

2. The composition of claim 1, wherein administration of the composition to a subject with Alzheimer's disease (AD) ameliorates symptoms of AD.

3. The composition of claim 1, wherein the one or more peptides further comprise one or more peptides having a cysteine residue on at least one end of the one or more peptides.

4. The composition of claim 1, wherein the one or more peptides include one or more derivatized amino acids, D-amino acids or combination thereof.

5. The composition of claim 1, wherein the one or more peptides are linked at an N- or C-terminus to a second polypeptide or protein to form one or more fusion peptides.

6. The composition of claim 1, wherein the one or more peptides are linked to a label or enzyme.

7. The composition of claim 1, wherein the one or more peptides consist of the amino acid sequence of SEQ ID NO: 13.

8. A composition comprising a peptide consisting of the amino acid sequence of SEQ ID NO: 13, and a pharmaceutically acceptable carrier.

9. A kit comprising:
   a. one or more peptides that bind to human amyloid-beta, wherein the one or more peptides comprise peptides comprising the amino acid sequence of SEQ ID NO: 13; and
   b. a container to contain the one or more peptides.

10. The kit of claim 9, further comprising Aβ42.

11. The kit of claim 10, further comprising a control peptide that does not bind to human amyloid-beta.

12. The kit of claim 9, wherein the one or more peptides consist of the amino acid sequence of SEQ ID NO: 13.

* * * * *

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Ala Ser Val Arg Gly Trp Tyr Val Arg Ser Val Phe Asp Pro Ala
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 2

Cys Ala Ser Val Arg Gly Trp Tyr Val Arg Ser Val Phe Asp Pro Ala
1               5                   10                  15
```

Cys

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 3

Ile Trp Gly Cys Ser Gly Lys Leu Ile Cys Thr Thr Ala Val Pro
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 4

Cys Ala Asp Trp Arg Tyr Arg Ser Val Phe Gly Pro Val Ser Val Ala
1               5                   10                  15

Cys

<210> SEQ ID NO 5
<211> LENGTH: 241
<212> TYPE: PRT
<213> ORGANISM: Artificial Sequence
<220> FEATURE:
<223> OTHER INFORMATION: Synthetic Peptide

<400> SEQUENCE: 5

Gln Val Lys Leu Gln Glu Ser Gly Thr Glu Val Val Lys Pro Gly Ala
1               5                   10                  15

Ser Val Lys Leu Ser Cys Lys Ala Ser Gly Tyr Ile Phe Thr Ser Tyr
                20                  25                  30

Asp Ile Asp Trp Val Arg Gln Thr Pro Glu Gln Gly Leu Glu Trp Ile
            35                  40                  45

Gly Trp Ile Phe Pro Gly Glu Gly Ser Thr Glu Phe Asn Glu Lys Phe
        50                  55                  60

Lys Gly Arg Ala Thr Leu Ser Val Asp Lys Ser Ser Ser Thr Ala Tyr
65                  70                  75                  80

Met Glu Leu Thr Arg Leu Thr Ser Glu Asp Ser Ala Val Tyr Phe Trp
                85                  90                  95

Ala Arg Gly Asp Tyr Tyr Arg Arg Tyr Phe Asp Leu Trp Gly Gln Gly
                100                 105                 110

Thr Thr Val Thr Val Ser Ser Gly Gly Ser Gly Gly Gly Gly
            115                 120                 125

Ser Gly Gly Gly Gly Ser Asp Ile Glu Leu Thr Gln Ser Pro Thr Ile
    130                 135                 140

Met Ser Ala Ser Pro Gly Glu Arg Val Thr Met Thr Cys Ser Ala Ser
145                 150                 155                 160

Ser Ser Ile Arg Tyr Ile Tyr Trp Tyr Gln Gln Lys Pro Gly Ser Ser
                165                 170                 175

Pro Arg Leu Leu Ile Tyr Asp Thr Ser Asn Val Ala Pro Gly Val Pro
            180                 185                 190

Phe Arg Phe Ser Gly Ser Gly Ser Gly Thr Ser Tyr Ser Leu Thr Ile
        195                 200                 205

Asn Arg Met Glu Ala Glu Asp Ala Ala Thr Tyr Tyr Cys Gln Glu Trp

```
                 210                 215                 220
Ser Gly Tyr Pro Tyr Thr Phe Gly Gly Thr Lys Leu Glu Leu Lys
225                 230                 235                 240

Arg

<210> SEQ ID NO 6
<211> LENGTH: 241
<212> TYPE: PRT
<213> ORGANISM: Artificial Sequence
<220> FEATURE:
<223> OTHER INFORMATION: Synthetic Peptide

<400> SEQUENCE: 6

Gln Val Lys Leu Gln Glu Ser Gly Thr Glu Val Val Lys Pro Gly Ala
1               5                   10                  15

Ser Val Lys Leu Ser Cys Lys Ala Ser Gly Tyr Ile Phe Thr Ser Tyr
                20                  25                  30

Asp Ile Asp Trp Val Arg Gln Thr Pro Glu Gln Gly Leu Glu Trp Ile
            35                  40                  45

Gly Trp Ile Phe Pro Gly Glu Gly Ser Thr Glu Phe Asn Glu Lys Phe
        50                  55                  60

Lys Gly Arg Ala Thr Leu Ser Val Asp Lys Ser Ser Ser Thr Ala Tyr
65                  70                  75                  80

Met Glu Leu Thr Arg Leu Thr Ser Glu Asp Ser Ala Val Tyr Phe Trp
                85                  90                  95

Ala Arg Gly Asp Tyr Tyr Arg Arg Tyr Phe Asp Leu Trp Gly Gln Gly
                100                 105                 110

Thr Thr Val Thr Val Ser Ser Gly Gly Gly Ser Gly Gly Gly
            115                 120                 125

Ser Gly Gly Gly Ser Asp Ile Glu Leu Thr Gln Ser Pro Thr Ile
        130                 135                 140

Met Ser Ala Ser Pro Gly Glu Arg Val Thr Met Thr Cys Ser Ala Ser
145                 150                 155                 160

Ser Ser Ile Arg Tyr Ile Tyr Trp Tyr Gln Gln Lys Pro Gly Ser Ser
                165                 170                 175

Pro Arg Leu Leu Ile Tyr Asp Thr Ser Asn Val Ala Pro Gly Val Pro
            180                 185                 190

Phe Arg Phe Ser Gly Ser Gly Ser Gly Thr Ser Tyr Ser Leu Thr Ile
        195                 200                 205

Asn Arg Met Glu Ala Glu Asp Ala Ala Thr Tyr Tyr Cys Gln Glu Trp
    210                 215                 220

Ser Gly Tyr Pro Tyr Thr Phe Gly Gly Thr Lys Leu Glu Leu Lys
225                 230                 235                 240

Arg

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 7

Gly Asp Tyr Tyr Arg Arg Tyr Phe Asp Leu
1               5                   10

<210> SEQ ID NO 8
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 8

Asp Arg Lys Gly Gly Ser Phe Asp Tyr
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Gln Arg Gly Asp Tyr
1               5

<210> SEQ ID NO 10
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 10

Ser Val Arg Gly Trp Tyr Val Arg Ser Val Phe Asp Pro
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Ser His Tyr Trp Asp Ser
1               5

<210> SEQ ID NO 12
<211> LENGTH: 240
<212> TYPE: PRT
<213> ORGANISM: Artificial Sequence
<220> FEATURE:
<223> OTHER INFORMATION: Synthetic Peptide

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Val Ser Ser Gly
            20                  25                  30

Asn Tyr Tyr Trp Thr Trp Ile Arg Gln Pro Pro Gly Lys Gly Leu Glu
        35                  40                  45

Trp Ile Gly Tyr Ile Tyr Ser Ser Gly Ser Thr Ser Tyr Asn Pro Ser
    50                  55                  60

Leu Met Ser Arg Val Thr Ile Ser Leu Asp Met Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Ser His Tyr Trp Asp Ser Trp Ser Pro Gly Thr Leu Val
            100                 105                 110
```

Thr Val Ser Gly Gly Gly Gly Ser Gly Gly Gly Ser Gly Gly
    115                 120                 125

Gly Gly Ser Asp Ile Val Met Thr Gln Ser Pro Ser Met Ser Ala
130                 135                 140

Ser Val Gly Asp Thr Val Thr Ile Ala Cys Arg Ala Ser Arg Asp Ile
145                 150                 155                 160

Arg Asn Asp Leu Ala Trp Tyr Gln Gln Lys Pro Gly Lys Ala Pro Lys
                165                 170                 175

Leu Leu Ile Tyr Ala Ala Ser Arg Leu Gln Ser Gly Val Pro Ser Arg
                180                 185                 190

Phe Ser Gly Ser Gly Ser Phe Thr Asp Phe Thr Leu Thr Ile Gln Leu
    195                 200                 205

Cys Leu Gln Pro Asp Asp Phe Ala Thr Tyr Tyr Cys Leu Gln Asp Ser
    210                 215                 220

Asp Tyr Pro Leu Thr Phe Gly Gly Gly Thr Lys Leu Glu Ile Lys Arg
225                 230                 235                 240

<210> SEQ ID NO 13
<211> LENGTH: 245
<212> TYPE: PRT
<213> ORGANISM: Artificial Sequence
<220> FEATURE:
<223> OTHER INFORMATION: Synthetic Peptide

<400> SEQUENCE: 13

Gln Ala Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Arg Gly Trp Tyr Val Arg Ser Val Phe Asp Pro Trp
            100                 105                 110

Ser Gln Gly Thr Leu Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Gly Ile Ser His His Leu Ala Trp Phe Gln Gln Lys
                165                 170                 175

Ala Gly Lys Ala Pro Lys Leu Leu Ile Tyr Gly Thr Ser Ser Leu Gln
            180                 185                 190

Ser Gly Val Pro Ser Arg Phe Ser Gly Ser Gly Ser Gly Thr Asp Phe
        195                 200                 205

Thr Leu Thr Asn Ser Ser Leu Gln Ser Glu Asp Phe Ala Thr Tyr Tyr
    210                 215                 220

Cys Leu Gln Asp Tyr Asn Phe Pro Tyr Thr Phe Gly Gln Gly Thr Lys

-continued

```
            225                 230                 235                 240
Leu Glu Ile Lys Arg
                245
```